United States Patent
Abe et al.

(10) Patent No.: US 10,745,432 B2
(45) Date of Patent: Aug. 18, 2020

(54) CRYSTAL OF 6'-SIALYLLACTOSE SODIUM SALT, AND PROCESS FOR PRODUCING SAME

(71) Applicant: KYOWA HAKKO BIO CO., LTD., Tokyo (JP)

(72) Inventors: Masahiro Abe, Tokyo (JP); Tomoya Yokoi, Tokyo (JP); Sotaro Sanpei, Tokyo (JP); Kazunari Fukumoto, Tokyo (JP); Hiroshi Nagano, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 0 days.

(21) Appl. No.: 15/769,025

(22) PCT Filed: Nov. 18, 2016

(86) PCT No.: PCT/JP2016/084282
§ 371 (c)(1),
(2) Date: Apr. 17, 2018

(87) PCT Pub. No.: WO2017/086443
PCT Pub. Date: May 26, 2017

(65) Prior Publication Data
US 2018/0305388 A1    Oct. 25, 2018

(30) Foreign Application Priority Data
Nov. 18, 2015   (JP) ................................ 2015-225652

(51) Int. Cl.
*C07H 5/06*   (2006.01)
*C07H 13/04*  (2006.01)
*C07H 1/00*   (2006.01)

(52) U.S. Cl.
CPC ................. *C07H 5/06* (2013.01); *C07H 1/00* (2013.01); *C07H 13/04* (2013.01); *C07B 2200/13* (2013.01)

(58) Field of Classification Search
CPC .. C07H 1/00; C07H 5/06; C07H 13/04; C07B 2200/13
USPC ........................................................ 536/53
See application file for complete search history.

(56) References Cited

U.S. PATENT DOCUMENTS

| 5,575,916 | A | 11/1996 | Brian et al. |
| 5,714,075 | A | 2/1998 | Brian et al. |
| 2012/0071441 | A1 | 3/2012 | Tamerlani et al. |
| 2013/0035481 | A1 | 2/2013 | Pérez Figueroa et al. |

FOREIGN PATENT DOCUMENTS

| JP | H08-252403 A | 10/1996 | |
| JP | H10-513437 A | 12/1998 | |
| JP | 2012-522761 A | 9/2012 | |
| JP | 2013-519694 A | 5/2013 | |
| WO | WO 2010/116317 A1 * | 10/2010 | ............. C07H 13/06 |
| WO | WO 2011/100979 A1 | 8/2011 | |

OTHER PUBLICATIONS

Caira, Mino R. Topics in Current Chemistry, Springer Verlag, 1998, 198, pp. 163-208.*
Japanese Patent Office, International Preliminary Report on Patentability in International Patent Application No. PCT/JP2016/084282 (dated May 22, 2018).
Drouillard et al., "Efficient synthesis of 6'-sialyllactose, 6,6'-disialyllactose, and 6'-KDO-lactose by metabolically engineered *E. coli* expressing a multifunctional sialyltransferase from the *Photobacterium* sp. JT-ISH-224," *Carbohydr. Res.*, 345(10): 1394-1399 (2010).
Rencurosi et al., "Human milk oligosaccharides: an enzymatic protection step simplifies the synthesis of 3'- and 6'-O-sialyllactose and their analogues," *Carbohydr. Res.*, 337: 473-483 (2002).
Japanese Patent Office, International Search Report in International Patent Application No. PCT/JP2016/084282 (dated Feb. 21, 2017).
Caira, "Crystalline Polymorphism of Organic Compounds," *Topics in Current Chemistry*, 198: 163-208 (1998).
European Patent Office, Extended European Search Report in European Patent Application No. 16866443.1 (dated Mar. 20, 2019).
Japan Chemical Society (editor), *Chemistry Experiment Course* (Fourth Edition, published by Maruzen Co., Ltd.), vol. 1, "Basic Operation 1," Sections 4.3.1 and 4.3.2, pp. 184-189 (Apr. 5, 1996).

* cited by examiner

*Primary Examiner* — Ganapathy Krishnan
(74) *Attorney, Agent, or Firm* — Leydig, Voit & Mayer, Ltd.

(57) ABSTRACT

An object of the present invention is to provide a crystal of 6'-sialyllactose (hereinafter, referred to as 6SL) sodium salt, which is easily handled, and has high storage stability at normal temperature as well as under high temperature conditions, and provide a production process thereof. The present invention relates to a crystal of 6SL sodium salt and a process for producing the crystal.

18 Claims, 8 Drawing Sheets

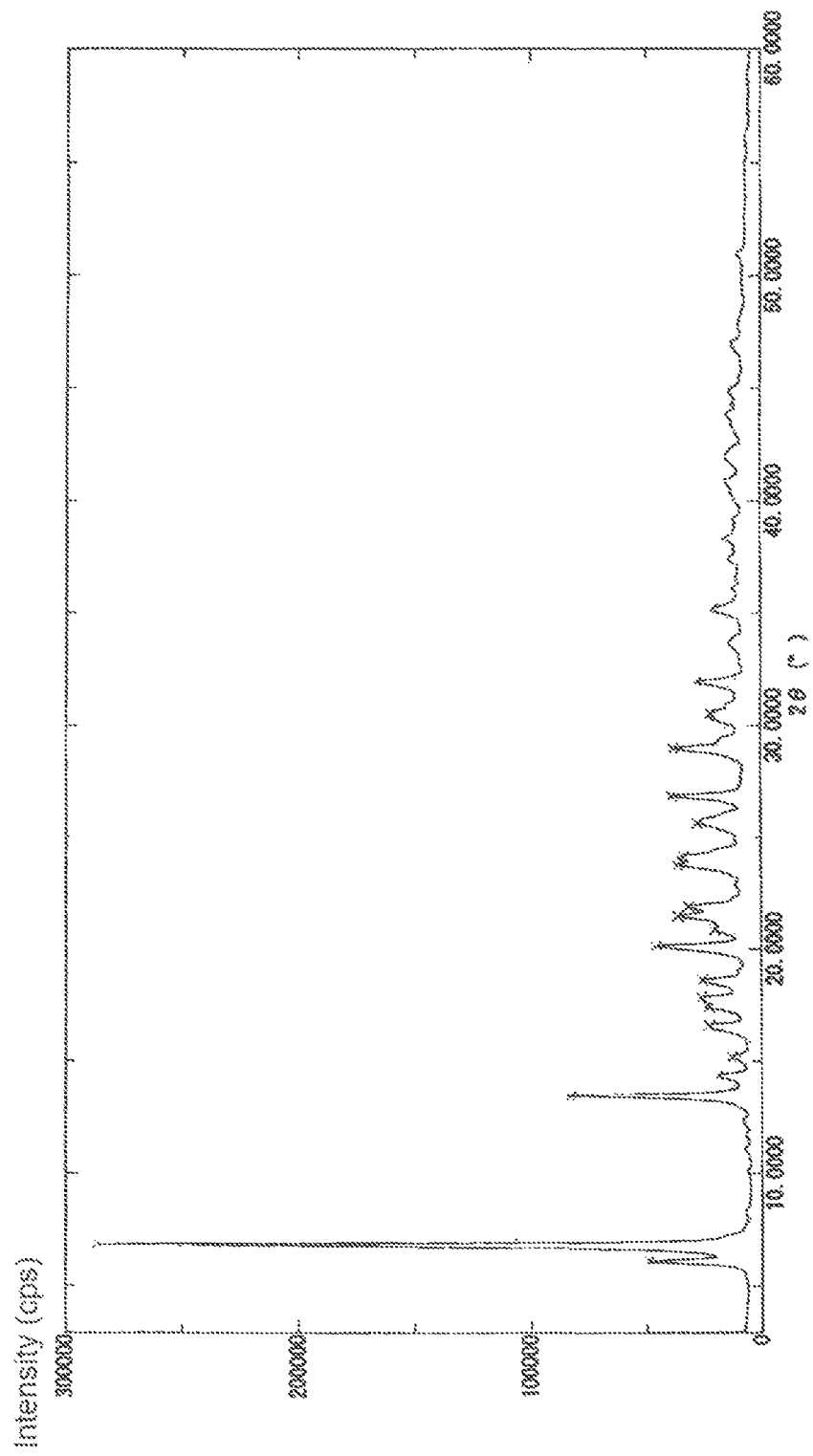

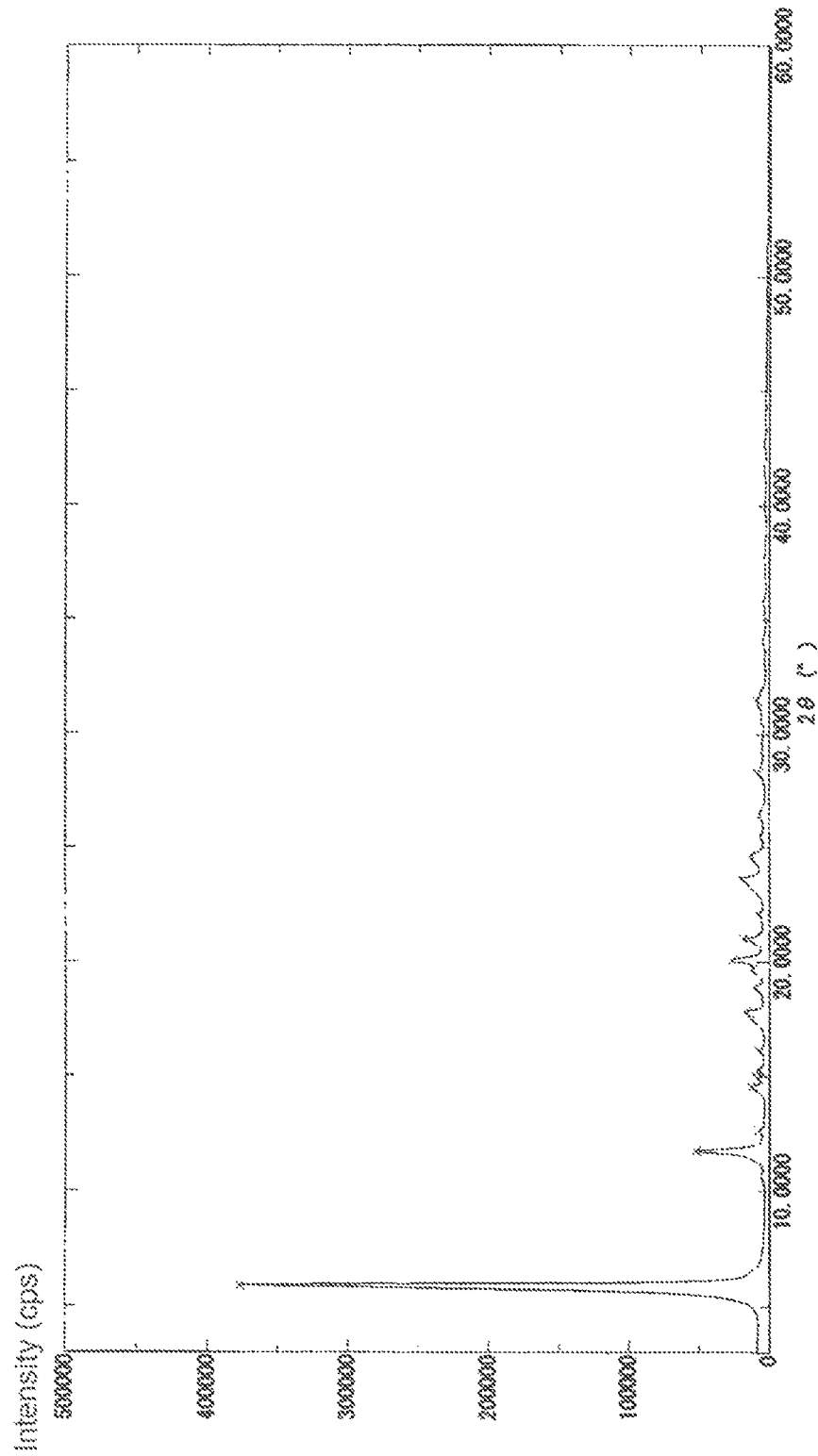

CRYSTAL OF 6'-SIALYLLACTOSE SODIUM SALT, AND PROCESS FOR PRODUCING SAME

CROSS-REFERENCE TO RELATED APPLICATIONS

This patent application is the U.S. national phase of International Patent Application No. PCT/JP2016/084282, filed Nov. 18, 2016, which claims the benefit of Japanese Patent Application No. 2015-225652, filed on Nov. 18, 2015, which are incorporated by reference in their entireties herein.

TECHNICAL FIELD

The present invention relates in a crystal of 6'-sialyllactose sodium salt, which is used, for example, as a product, a raw material, an intermediate, or the like of health food, pharmaceuticals, cosmetics, and the like, and a production process of the crystal.

BACKGROUND ART

6'-Sialyllactose [O—(N-acetyl-α-neuramionsyl)-(2→6)—O-β-D-galactopyranoyl-(1→4)-D-Glucose](hereinafter, referred to as 6SL) is an acidic oligosaccharide in which sialic acid is linked to lactose.

6SL is useful, for example, as a product, a raw material, an intermediate, or the like of health food, pharmaceuticals, cosmetics, and the like. 6SL is one of important oligosaccharides contained in human breast milk and is supposed to have a bioactivity such as a protective activity against infection with a virus or a bacterium, or an activity of lactic acid bacterial growth.

As a method for purifying 6SL, a method using a gel filtration column (Non-Patent Documents 1 and 2), a simulated moving-bed chromatographic separation device (Patent Document 1), or the like has been disclosed. Further, Patent Documents 2 to 4 describe that a crystal of 6SL salt was obtained, but do not describe the properties of the obtained crystals, and a method by which a crystal of 6SL salt can actually be obtained has not been known.

RELATED ART

Patent Document

Patent Document 1: JP-A-08-252403
Patent Document 2: JP-T-10-513437
Patent Document 3: WO 2010/11631
Patent Document 4: WO 2011/100979

Non-Patent Document

Non-Patent Document 1: Carbohydrate Research., Vol. 337, p. 473, 2002
Non-Patent Document 2: Carbohydrate Research., Vol. 345, p. 1394, 2010

SUMMARY OF THE INVENTION

Problems to be Solved by the Invention

An object of the present invention is to provide a crystal of 6SL, which is easily handled, and has high storage stability at normal temperature as well as under high temperature conditions, and provide a production process thereof.

Means for Solving the Problems

The present invention relates to the following (1) to (21).
(1) A crystal of 6'-sialyllactose (hereinafter, referred to as 6SL) sodium salt.
(2) The crystal described in (1) above, wherein the crystal is a crystal of 6SL sodium sale n-hydrate (wherein n represents an arbitrary number of 0 to 5, and when n is 0, it is referred to as 6SL sodium salt hydrate).
(3) The crystal described in (2) above, wherein the crystal has peaks at diffraction angles (2θ) of 6.7±0.2°, 13.3±0.2°, 17.7±0.2°, 18.5±0.2°, and 20.0±0.2° in powder X-ray diffraction.
(4) The crystal described in (3) above, wherein the crystal further has peaks at diffraction angles (2θ) of 16.5±0.2°, 21.3±0.2°, 21.8±0.2°, 23.6±0.2°, and 28.8±0.2° in powder X-ray diffraction.
(5) The crystal described in (4) above, wherein the crystal further has peaks at diffraction angles (2θ) of 17.3±0.2°, 23.9±0.2°, 24.0±0.2°, 25.7±0.2°, and 26.7±0.2° in powder X-ray diffraction.
(6) A process for producing a crystal of 6SL sodium salt n-hydrate or a solvate crystal of 6SL sodium salt n-hydrate (wherein n has the same meaning as in (2) above), comprising a step of dissolving amorphous 6SL sodium salt in an alcohol solution, a step of precipitating a crystal of 6SL sodium salt n-hydrate or a solvate crystal of 6SL sodium salt n-hydrate by leaving the solution to stand or stirring the solution, and a step of collecting the crystal of 6SL sodium salt n-hydrate or the solvate crystal of 6SL sodium salt n-hydrate from the solution.
(7) A process for producing a crystal of 6SL sodium salt n-hydrate or solvate crystal of 6SL sodium salt n-hydrate (wherein n has the same meaning as in (2) above), comprising a step of adding a crystal of 6SL sodium salt n-hydrate as a seed crystal to a 6SL aqueous solution containing a sodium-containing compound, a step of precipitating a crystal of 6SL sodium salt n-hydrate or a solvate crystal of 6SL sodium salt n-hydrate in the aqueous solution, and a step of collecting the crystal of 6SL sodium salt n-hydrate or the solvate crystal of 6SL sodium salt n-hydrate from the aqueous solution.
(8) The production process described in (7) above, wherein the step of precipitating a crystal of 6SL sodium salt n-hydrate or a solvate crystal of 6SL sodium salt n-hydrate in the aqueous solution is a step of precipitating the crystal of 6SL sodium salt n-hydrate or the solvate crystal of 6SL sodium salt n-hydrate by adding or adding dropwise an alcohol solution to the aqueous solution.
(9) The production process described in any one of (6) to (8) above, further comprising a step of drying the crystal of 6SL sodium salt n-hydrate or the solvate crystal of 6SL sodium salt n-hydrate.
(10) The production process described in any one of (6) to (9) above, wherein the crystal of 6SL sodium salt n-hydrate is a crystal of 6SL sodium salt n-hydrate described in any one of the following (i) to (iii):
(i) a crystal of 6SL sodium salt n-hydrate which has peaks at diffraction angles (2θ) of 6.7±0.2°, 13.3±0.2°, 17.7±0.2°, 18.5±0.2°, and 20.0±0.2° in powder X-ray diffraction;
(ii) a crystal of 6SL sodium salt n-hydrate which further has peaks at diffraction angles (2θ) of 16.5±0.2°, 21.3±0.2°, 21.8±0.2°, and 28.8±° in addition to the peaks at the diffraction angles (2θ) described in (i) in powder X-ray diffraction; and (iii) a crystal of 6SL sodium salt n-hydrate which further has peaks at diffraction angles (2θ) of 17.3±0.2°, 23.9±0.2°, 24.0±0.2°, 25.7±0.2°, and 26.7±0.2° in addition to the peaks at the diffraction angles (2θ) described in (i) and (ii) in powder X-ray diffraction.

(11) The production process described in any one of (6) and (8) to (10) above, wherein the alcohol solution is a solution of C1-C6 alcohol.

(12) The production process described in (11) above, wherein the C1-C6 alcohol is methanol.

(13) The production process described in (12) above, wherein the solvate crystal of 6SL sodium salt n-hydrate is a crystal of 6SL sodium salt 2.5-hydrate 0.5-methanol solvate.

(14) The Crystal described in (2) above, wherein the crystal has peaks at diffraction angles (2θ) of 5.9±0.2°, 11.7±0.2°, 20.1±0.2°, and 23.6±0.2° in powder X-ray diffraction.

(15) The crystal described in (14) above, wherein the crystal further has peaks at diffraction angles (2θ) of 17.8±0.2°, 14.5±0.2°, 17.4±0.2°, 19.7±0.2°, and 24.6±0.2° in powder X-ray diffraction.

(16) The crystal described in (15) above, wherein the crystal further has peaks at diffraction angles (2θ) of 14.9±0.2°, 18.9±0.2°, 22.1±0.2°, 28.3±0.2°, 28.3±0.2°, and 31.5±0.2° in powder X-ray diffraction.

(17) A process for producing a crystal of 6SL sodium salt n-hydrate (wherein n has the same meaning as in (2) above), comprising a step of dissolving N,N-dimethylformamide in a 6SL aqueous solution containing a sodium-containing compound to precipitate a crystal of 6SL sodium salt n-hydrate in the aqueous solution, and a step of collecting the crystal of 6SL sodium salt n-hydrate from the aqueous solution.

(18) A process for producing a crystal of 6SL sodium salt n-hydrate (wherein n has the same meaning as in (2) above), comprising a step of adding a crystal of 6SL sodium salt n-hydrate as a seed crystal to 6SL aqueous solution containing a sodium-containing compound, a step of precipitating a crystal of 6SL sodium salt n-hydrate by adding or adding dropwise N,N-dimethylformamide to the aqueous solution.

(19) The production process described in (17) to (18) above, wherein the crystal of 6SL sodium salt n-hydrate is a crystal of 6SL sodium salt n-hydrate described in any one of the following (iv) to (vi):

(iv) a crystal of 6SL sodium salt n-hydrate which has peaks at diffraction angles (2θ) of 5.9±0.2°, 11.7±0.2°, 20.1±0.2°, 21.0±0.2°, and 23.6±0.2° in powder X-ray diffraction;

(v) a crystal of 6SL sodium salt n-hydrate which further has peaks at diffraction angles (2θ) of 17.8±0.2°, 14.5±0.2°, 17.4±0.2°, 19.7±0.2°, and 24.6±0.2° in addition to the peaks at the diffraction angles (2θ) described in (iv) in powder X-ray diffraction; and (vi) a crystal of 6SL sodium salt n-hydrate which further has peaks at diffraction angles (2θ) of 14.9±0.2°, 18.9±0.2°, 22.1±0.2°, 28.3±0.2°, and 31.5±0.2° in addition to the peaks at the diffraction angles (2θ) described in (iv) and (v) in powder X-ray diffraction.

(20) The crystal described in (1) above, wherein the crystal is a crystal of 6SL sodium salt 2.5-hydrate 0.5-methanol solvate.

(21) The crystal described in (20) above, wherein the crystal has the following approximate unit cell parameters when measured at −173° C. in single crystal X-ray structure analysis: a=9.0695 Å; b=12.4146 Å; c=14.6177 Å; α=71.326°; β=79.972°; γ=14.6177°; V=15.33.3 Å³; and Z=1, and has a space group of P1.

Effects of the Invention

According to the present invention, a crystal of 6SL, which is easily handled, and has high storage stability at normal temperature as well as under high temperature conditions, and a production process thereof are provided.

BRIEF DESCRIPTION OF THE DRAWINGS

FIG. 7 illustrates the results of powder X-ray diffraction of a crystal of 6SL sodium salt 2.7-hydrate obtained in Example 5.

FIG. 8 illustrates the results of powder X-ray diffraction of a crystal of 6SL sodium salt 2.3-hydrate obtained in Example 7.

MODE FOR CARRYING OUT THE INVENTION

1. Crystal of the Present Invention

Figure 1:
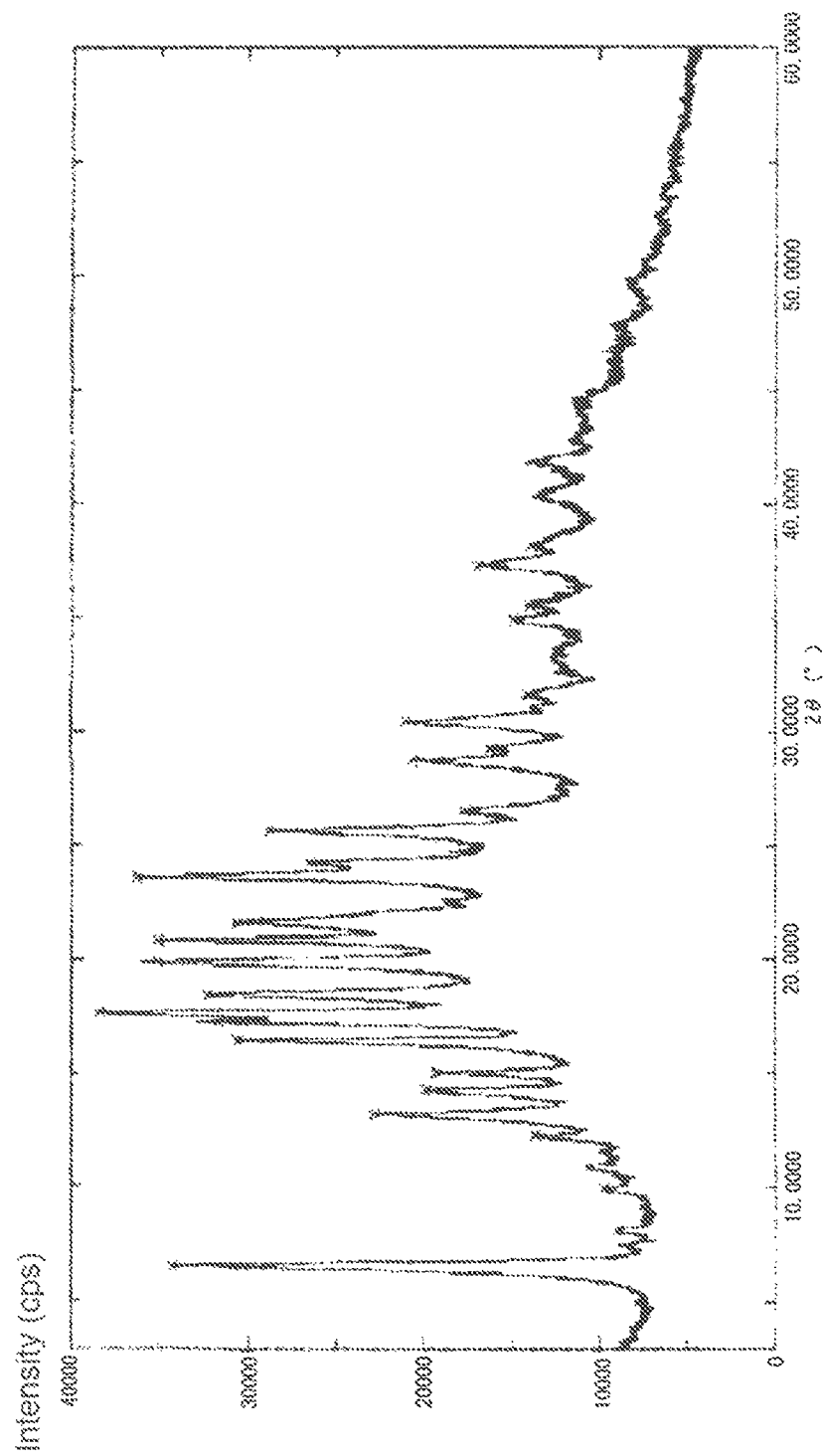
FIG. 1 illustrates the results of powder X-ray diffraction of a crystal of 6SL sodium salt 4.0-hydrate obtained in Example 1.

The crystal of the present invention is a crystal of 6SL sodium salt.

The crystal of the present invention includes a crystal of 6SL sodium salt n-hydrate (wherein n is an arbitrary number of 0 to 5, preferably an arbitrary number which is larger than 0 but 5 or smaller, more preferably an arbitrary number which is larger than 0 but 5 or smaller and is shown to one decimal place, and when n is 0, it is referred to as 6SL sodium salt anhydrate), and a solvate crystal of 6SL sodium salt n-hydrate.

Whether the crystal of the present invention is a crystal of 6SL can be confirmed by a method using HPLC described later in Analysis Examples.

Whether the crystal of the parent invention is a crystal of a sodium salt can be confirmed by measuring the content of sodium contained in the crystal using an atomic absorption spectrophotometer described later in Analysis Examples.

For example, the crystal of the present invention can be confirmed to be a crystal of monosodium salt by the fact that the sodium content in the crystal is generally 3.5±1.0 wt %, preferably 3.5±0.5 wt %, most preferably 3.5±0.3 wt %.

The crystal of the present invention can be confirmed to be a crystal of n-hydrate by the fact that the water content as measured using the Karl-Fisher method described later in Analysis Examples is generally from 0.0 to 12.0 wt %.

The solvate crystal of 6SL sodium salt n-hydrate may be any as long as it is formed from water and one or more kinds of solvents other than water, and is preferably a crystal formed from water and one solvent other than water. The solvent other than water which constitutes the solvent crystal formed from water and one or more kinds of solvents other than water may include an alcohol (for example, methanol, ethanol, propanol, isopropanol, or the like), and may preferably include methanol.

In the present invention, for example, in a case where the crystal is "a solvate crystal formed from water and a solvent other than water", the crystal is represented by "a hydrate solvate crystal", in a case where the crystal is "a solvate crystal formed from water and methanol", the crystal is represented by "a hydrate methanol solvate crystal", and so on.

In the hydrate solvate crystal formed from water and one or more kinds of solvents, it is preferred that the molar ratio of the total amount of water and the solvents with respect to one mol of 6SL sodium salt is generally set to 0.6 mol to 6 mol. In the hydrate solvate crystal formed from water and one or more kinds of solvents, the constituent ratio of water to the solvent is not particularly limited, and for example, in a case of a hydrate alcohol solvate crystal, it is preferred that the ratio is set within the following range: water:alcohol=0.5:1 to 50:1.

As the hydrate solvate crystal formed from water and one or more kinds of solvents, a hydrate methanol solvate crystal is preferred, and specific examples thereof include a crystal of 0.5 to 5-hydrate 0.1 to 1-methanol solvate, and a crystal of 2.5-hydrate 0.5-methanol solvate is particularly preferred.

Figure 2:
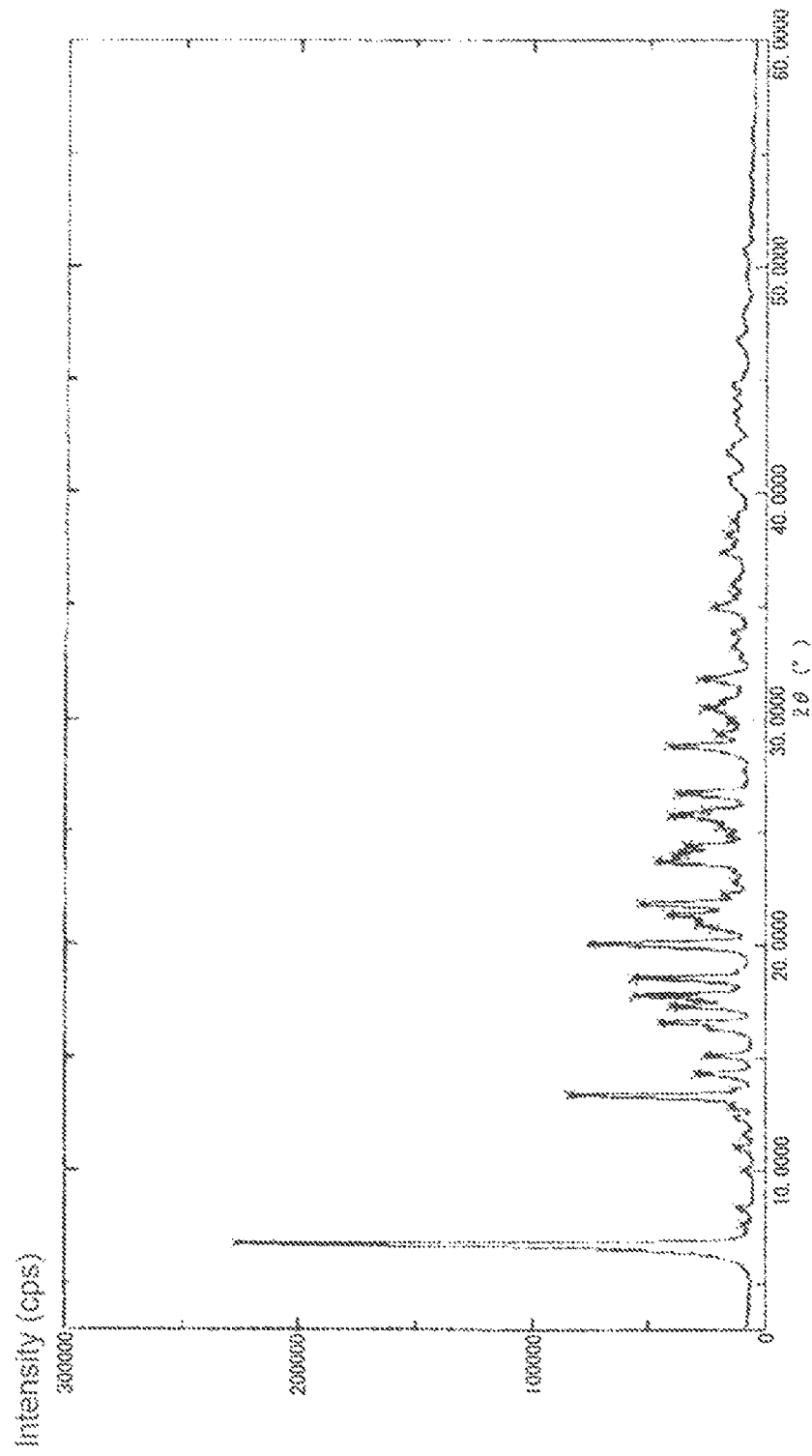
FIG. 2 illustrates the results of powder X-ray diffraction of a crystal of 6SL sodium salt 4.6-hydrate obtained in Example 2.
Figure 5:
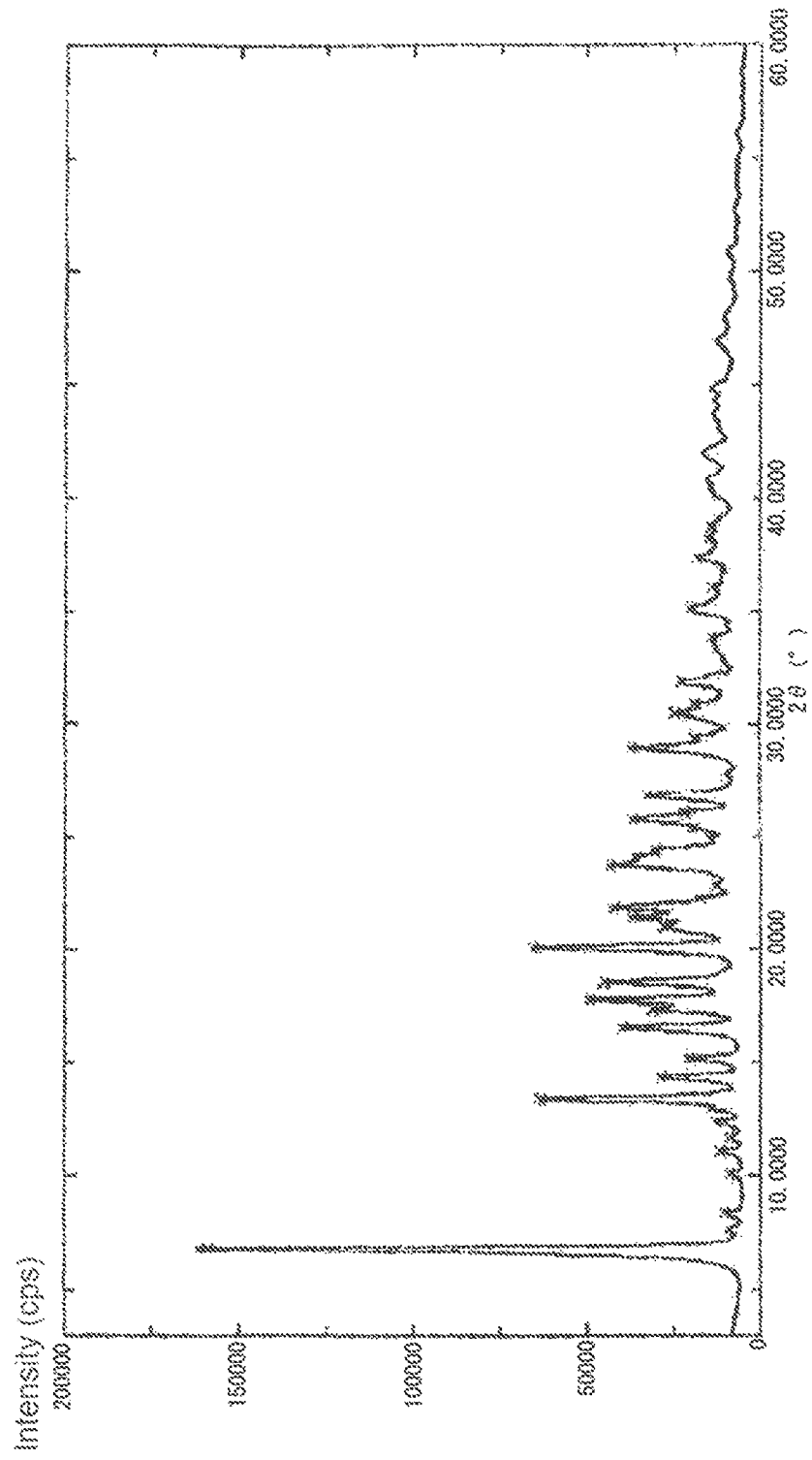
FIG. 5 illustrates the results of powder X-ray diffraction of a crystal of 6SL sodium salt 3.3-hydrate obtained in Example 3.

The crystal of 6SL sodium salt n-hydrate of the present invention may include a crystal of 6SL sodium salt 4.0-hydrate whose powder X-ray diffraction pattern using CuKα as the X-ray source is defined by the values shown in FIG. 1 and Table 1, a crystal of 6SL sodium salt 4.6-hydrate whose powder X-ray diffraction pattern is defined by the values shown in FIG. 2 and Table 2, a crystal of 6SL sodium salt 3.3-hydrate whose powder X-ray diffraction pattern is defined by the values shown in FIG. 5 and Table 6, a crystal of 6SL sodium salt 2.7-hydrate whose powder X-ray diffraction pattern is defined by the values shown in FIG. 7 and Table 8, and a crystal of 6SL sodium salt 2.3-hydrate whose powder X-ray diffraction pattern is defined by the value, shown in FIG. 8 and Table 9.

Further, the crystal of 6SL sodium salt n-hydrate of the present invention may include a crystal of 6SL sodium salt 4.6-hydrate which shows the infrared absorption spectrum illustrated in FIG. 3 when subjected to the infrared spectroscopic (IR) analysis described later in Analysis Examples.

The crystal of 6SL sodium salt n-hydrate of the present invention is specifically preferably a crystal of 6SL sodium salt n-hydrate which has peaks at diffraction angles (2θ) described in the following (i) in powder X-ray diffraction using CuKα as the X-ray source, more preferably a crystal of 6SL sodium salt n-hydrate which further has peaks at diffraction angles (2θ) described in the following (ii) in addition to the diffraction angles (2θ) described in the following (i), and further more preferably a crystal of 6SL sodium salt n-hydrate which further has peaks at diffraction angles (2θ) described in the following (iii) in addition to the diffraction angles (2θ) described in the following (i) and (ii).

(i) 6.7±0.2°, preferably 6.7±0.1°, 13.3±0.2°, preferably 13.3±0.2°, 17.7±0.2°, preferably 17.7±0.1°, 18.5±0.2°, preferably 18.5±0.1°, and 20.0±0.2° preferably 20.0±0.1°

(ii) 16.5±0.2°, preferably 16.5±0.1°, 21.3±0.2°, preferably 21.3±0.1°, 21.8±0.2°, preferably 21.8±0.1°, 23.6±0.2°, preferably 23.6±0.1°, and 28.8±0.2° preferably 28.8±0.1°

(iii) 17.3±0.2°, preferably 17.3±0.1°, 23.9±0.2°, preferably 23.9±0.1°, 24.0±0.2°, preferably 24.0±0.1°, 25.7±0.2°, preferably 25.7±0.1°, and 26.7±0.2° preferably 26.7±0.1°

In addition, the crystal of 6SL sodium salt n-hydrate of the present invention is specifically preferably a crystal of 6SL sodium salt n-hydrate which has peaks at diffraction angle (2θ) described in following (iv) in powder X-ray diffraction using CuKα as the X-ray source, more preferably a crystal of 6SL sodium salt n-hydrate which further has peaks at diffraction angles (2θ) described in the following (v) in addition to the diffraction angles (2θ) described in the following (iv), and further more preferably a crystal of 6SL sodium salt n-hydrate which further has peaks at diffraction angles (2θ) described in the following (vi) in addition to the diffraction angles (2θ) described in the following (iv) and (v).

(iv) 5.9±0.2°, preferably 5.9±0.1°, 11.7±0.2°, preferably 11.7±0.1°, 20.1±0.2°, preferably 20.1±0.1°, 21.0±0.2°, preferably 21.0±0.1°, and 23.6±0.2° preferably 23.6±0.1°

(v) 17.8±0.2°, preferably 17.8±0.1°, 14.5±0.2°, preferably 14.5±0.1°, 17.4±0.2°, preferably 17.4±0.1°, 19.7±0.2°, preferably 19.7±0.1°, and 24.6±0.2°, preferably 24.6±0.1°

(vi) 14.9±0.2°, preferably 14.9±0.1°, 18.9±0.2°, preferably 18.9±0.1°, 22.1±0.2°, preferably 22.1±0.1°, 28.3±0.2°, preferably 28.3±0.1°, and 31.5±0.2°, preferably 31.5±0.1°

The solvate crystal of 6SL sodium salt n-hydrate of the present invention may include a crystal of 6SL sodium salt 2.5-hydrate 0.5-methanol solvate defined by the values shown in Table 7 in single crystal X-ray structure analysis.

Further, the solvate crystal of 6SL sodium salt n-hydrate of the present invention specifically includes a crystal of 6SL sodium salt n-hydrate 0.5-methanol solvate which has the following approximate unit cell parameters when measured at −173° C. in single crystal X-ray structure analysis: a=9.0695 Å; b=12.4146 Å; c=14.6177 Å; α=71.326°; β=79.972°; γ=14.6177°; V=1533.3 Å$^3$; and Z=1, and has a group of P1.

2. Process for Producing Crystal of the Present Invention

The process for producing the crystal of the present invention (hereinafter also referred to as "process of the present invention") includes the following production processes described in 2.1 to 2.3.

2.1 Process for Producing Crystal of the Present Invention (1)

The process for producing the crystal of the present invention may include a process for producing a crystal of 6SL sodium salt n-hydrate or a solvate based of 6SL sodium salt n-hydrate, comprising a step of dissolving an amorphous 6SL sodium salt in an alcohol solution, a step of precipitating a crystal of 6SL sodium salt n-hydrate or a solvate crystal of 6SL sodium salt n-hydrate by leaving the solution to stand or stirring the solution, and a step of collecting the crystal of 6SL sodium salt n-hydrate or the solvate crystal of 6SL sodium salt n-hydrate from the solution.

The alcohol solution may be a mixture of a plurality of kinds of alcohols, or a mixture of an alcohol and another organic solvent or water so far as it can be used in the process of the present invention, and may be preferably a C1-C6 alcohol, more preferably a C1-C3 alcohol, further more preferably an alcohol selected from the group consisting of methanol, ethanol, n-propanol, and isopropyl alcohol, still further more preferably methanol or ethanol, most preferably methanol.

Further, in a case where the alcohol solution used in the process of the present invention is an alcohol aqueous solution, the water content may be generally 40 wt % or less, preferably 20 wt % or less, more preferably 10 wt % or less, most preferably 5 wt % or less.

A method for dissolving amorphous 6SL sodium salt in the alcohol solution may include, for example, a method in winch amorphous 6SL sodium salt is suspended in the solution, followed by filtering the resulting solution, whereby a filtrate is obtained.

Amorphous 6SL sodium salt can be obtained by, for example, the method described later in Reference Examples.

The solution obtained by dissolving amorphous 6SL sodium salt is left to stand or stirred, whereby a crystal of 6SL sodium salt n-hydrate or a solvate crystal of 6SL sodium salt n-hydrate can be precipitated. The temperature at which the solution is left to stand or stirred may be generally from 0 to 80° C., preferably from 5 to 50° C. most preferably from 10 to 30° C.

The time for which the solution is left to stand or stirred may be generally from 1 to 100 hours, preferably from 3 to 48 hours, most preferably from 5 to 24 hours.

The method for collecting the crystal of 6SL sodium salt n-hydrate or the solvate crystal of 6SL sodium salt n-hydrate is not particularly limited but may include, for example, collection by filtration, pressure filtration, suction filtration, centrifugal separation, and the like. Furthermore, in order to reduce the adhesion of the mother liquid to the crystal and thereby improve the quality of the crystal, the crystal may be appropriately washed after collecting the crystal.

The solution used for crystal washing is not particularly limited, but water, methanol, ethanol, acetone, n-propanol, isopropyl alcohol, and a solution prepared by mixing one kind or a plurality of kinds of members selected from these at an arbitrary ratio may be used.

The thus obtained wet crystal is dried, whereby the crystal of the present invention can be obtained. That is, the process for producing the crystal of the present invention may further include a step of drying the crystal of 6SL sodium salt n-hydrate or the solvate crystal of 6SL sodium salt n-hydrate.

As for the drying conditions, any method may be used as long as the form of the crystal of 6SL sodium salt n-hydrate or the solvate crystal of 6SL sodium salt n-hydrate can be maintained, and for example, reduced-pressure drying, vacuum drying, fluidized bed drying, forced air drying, and the like may be applied.

The drying temperature may be any temperature as long as the adhered water or solution can be removed, but the temperature may be preferably 80° C. or less, mom preferably 60° C. or less.

By employing the above-mentioned process, a high-purity crystal of 6SL sodium salt n-hydrate or a high-purity solvate crystal of 6SL sodium salt n-hydrate can be obtained. The purity of the crystal may be generally 97% or more, preferably or more, more preferably 99% or more, most preferably 99.5% or more.

The crystal of the present invention, which can be produced by the above-mentioned production process, may include, for example, a crystal of 6SL sodium salt 4.0-hydrate whose powder X-ray diffraction pattern using CuKα as the X-ray source is defined by the values shown in FIG. 1 and Table 1.

2.2 Process for Producing Crystal of the Present Invention (2)

Also, the process for producing the crystal of the present invention may include a process for producing a crystal of 6SL sodium salt n-hydrate or a solvate crystal of 6SL sodium salt n-hydrate, comprising a step of adding a crystal of 6SL sodium salt n-hydrate as a seed crystal to a 6SL aqueous solution containing a sodium-containing compound, a step of precipitating a crystal of 6SL sodium salt n-hydrate or a solvate crystal of 6SL sodium salt n-hydrate in the aqueous solution, and a step of collecting the crystal of 6SL sodium salt n-hydrate or the solvate crystal of 6SL sodium salt n-hydrate from the aqueous solution.

6SL contained in the 6SL sodium salt aqueous solution may be produced by any of a fermentation method, an enzyme method, an extraction method from a natural product, a chemical synthesis method, and other production methods.

In a case where a solid material that obstructs crystallization is contained in the 6SL aqueous solution, the solid material can be removed using centrifugal separation, filtration, a ceramic filter, or the like. In a case where a water-soluble impurity or salt that obstructs crystallization is contained in the 6SL aqueous solution, the water-soluble impurity or salt can be removed by passing the aqueous solution through a column packed with an ion exchange resin, or the like.

Further, in a case where a hydrophobic impurity that obstructs crystallization is contained in the 6SL aqueous solution, the hydrophobic impurity can be removed by passing the aqueous solution through a column packed with a synthetic adsorption resin, active carbon, or the like.

The aqueous solution can be prepared such that the concentration 6SL is generally 300 g/L or more, preferably 400 g/L or more, more preferably 500 g/L or more most preferably 600 g/L or more. In order to adjust the concentration in the aqueous solution to the concentration above, the aqueous solution can be concentrated in a general concentration method such as a heating concentration method or vacuum concentration method.

The sodium-containing compound may include, for example, a basic compound such as a sodium hydroxide aqueous solution, or a neutral salt such as a carbonate of sodium, a sulfate sodium, a nitrate of sodium, or a chloride of sodium. The neutral salt may include, for example, sodium carbonate, sodium sulfate, sodium nitrate, or sodium chloride.

In a case where a basic confound is used as the sodium-containing compound, the 6SL aqueous solution containing a sodium-containing compound and having a pH of generally 3.0 to 9.0, preferably 4.5 to 8.5, most preferably 5.5 to 8.0, can be obtained by adjusting the pH of the 6SL aqueous solution using the basic compound.

A crystal of 6SL sodium salt n-hydrate is added as a seed crystal to the 6SL aqueous solution containing a sodium-containing compound. As the crystal of 6SL sodium salt n-hydrate added as a seed crystal, the crystal obtained by the process of the present invention can be used.

The seed crystal may be added before the step of precipitating the crystal of may be added in the step of precipitating the crystal as long as it is added before the crystal of 6SL sodium salt n-hydrate or the solvate crystal of 6SL sodium salt n-hydrate is precipitated in the aqueous solution.

The seed crystal is added so that the concentration in the aqueous solution is generally from 0.2 to 15 wt %, preferably from 0.5 to 10 wt %, most preferably from 2 to 7 wt %.

The method for precipitating the crystal of 6SL sodium salt n-hydrate or the solvate crystal of 6SL sodium sale n-hydrate in the aqueous solution may include, for example, a method in which the aqueous solution is cooled, a method in which the aqueous solution is vacuum-concentrated, a method in which an alcohol solution or N,N-dimethylformamide is added or added dropwise to the aqueous solution, and the like. Further, one or more methods of these methods may be combined and used.

In the method in which the aqueous solution is cooled, the temperature of the aqueous solution may be generally from 0 to 50° C., preferably from 0 to 30° C., most preferably from 0 to 10° C., and the cooling time may be generally from 2 to 100 hours preferably from 3 to 50 hours, most preferably from 5 to 30 hours.

In the method in which the aqueous solution is vacuum-concentrated, the temperature of the aqueous solution may be generally from 0 to 100° C.; preferably from 10 to 90° C., most preferably from 20 to 80° C., and the vacuuming time may be generally from 1 to 120 hours, preferably from to 60 hours, most preferably from 3 to 50 hours.

In the method in which an alcohol solution or N,N-dimethylformamide is added or added dropwise to the aqueous solution whereby the crystal of 6SL sodium salt n-hydrate or the solvate crystal of 6SL sodium salt n-hydrate is precipitated in the aqueous solution, a seed crystal may be added after the addition or dropwise addition of an alcohol solution is started and before the crystal of 5SL sodium salt n-hydrate or the solvate crystal of 6SL sodium salt n-hydrate is precipitated.

The time as which the seed crystal is added after the addition or dropwise addition of an alcohol solution or N,N-dimethylformamide is started may be generally at 0 to 5 hours, preferably at 0 or 4 hours, most preferably at 0 to 3 hours after the addition or dropwise addition of an alcohol solution or N,N-dimethylformamide is started.

The alcohol solution may include the same examples as described in the above 2.1.

The temperature of the aqueous solution when the alcohol solution or N,N-dimethylformamide is added or added dropwise may be any temperature as long as 6SL is not decomposed, but in order to decrease the degree of solubility and thereby enhance the crystallization rate of the crystal of 6SL sodium salt n-hydrate or the solvate crystal of 6SL sodium salt n-hydrate, the temperature may be generally 80° C. or less, preferably 70° C. or less, more preferably 60° C. or less, most preferably 50° C. or less. The lower limit of the temperature may be generally 0° C. or more, preferably 10° C. or more.

The liquid amount of the alcohol solution or N,N-dimethylformamide to be added or added dropwise may be generally from 1 to 30 times, preferably from 2 to 25 times, most preferably from 3 to 10 times the amount of the aqueous solution. The time for which the alcohol solution is added or added dropwise may be generally from 1 to 48 hours, preferably from 2 to 30 hours, most preferably from 3 to 30 hours.

After the crystal of 6SL sodium salt n-hydrate or the solvate crystal of 6SL sodium salt n-hydrate is precipitated as described above, the precipitated crystal may be further matured generally for 1 to 72 hours, preferably for 1 to 48 hours, most preferably for 1 to 24 hours before the step of collecting the precipitated crystal.

The word "mature" means to grow the crystal by once stopping the step of precipitating the crystal of 6SL sodium salt n-hydrate or the solvate crystal of 6SL sodium salt n-hydrate. After the crystal is matured, the step of precipitating the crystal of 6SL sodium salt n-hydrate or the solvate crystal of 6SL sodium salt n-hydrate may be resumed.

The method for collecting the crystal of 6SL sodium salt n-hydrate or the solvate crystal of 6SL sodium salt n-hydrate may include the same method as described in the above 2.1.

By the above-mentioned process, a high-purity crystal of 6SL sodium salt n-hydrate or a high-purity solvate crystal of 6SL sodium salt n-hydrate can be obtained. The purity of the crystal of 6SL sodium salt n-hydrate or the solvate crystal of 6SL sodium salt n-hydrate may be generally 97% or more, preferably 98% or more, more preferably 99% or more, most preferably 99.5%, or more.

Figure 3:
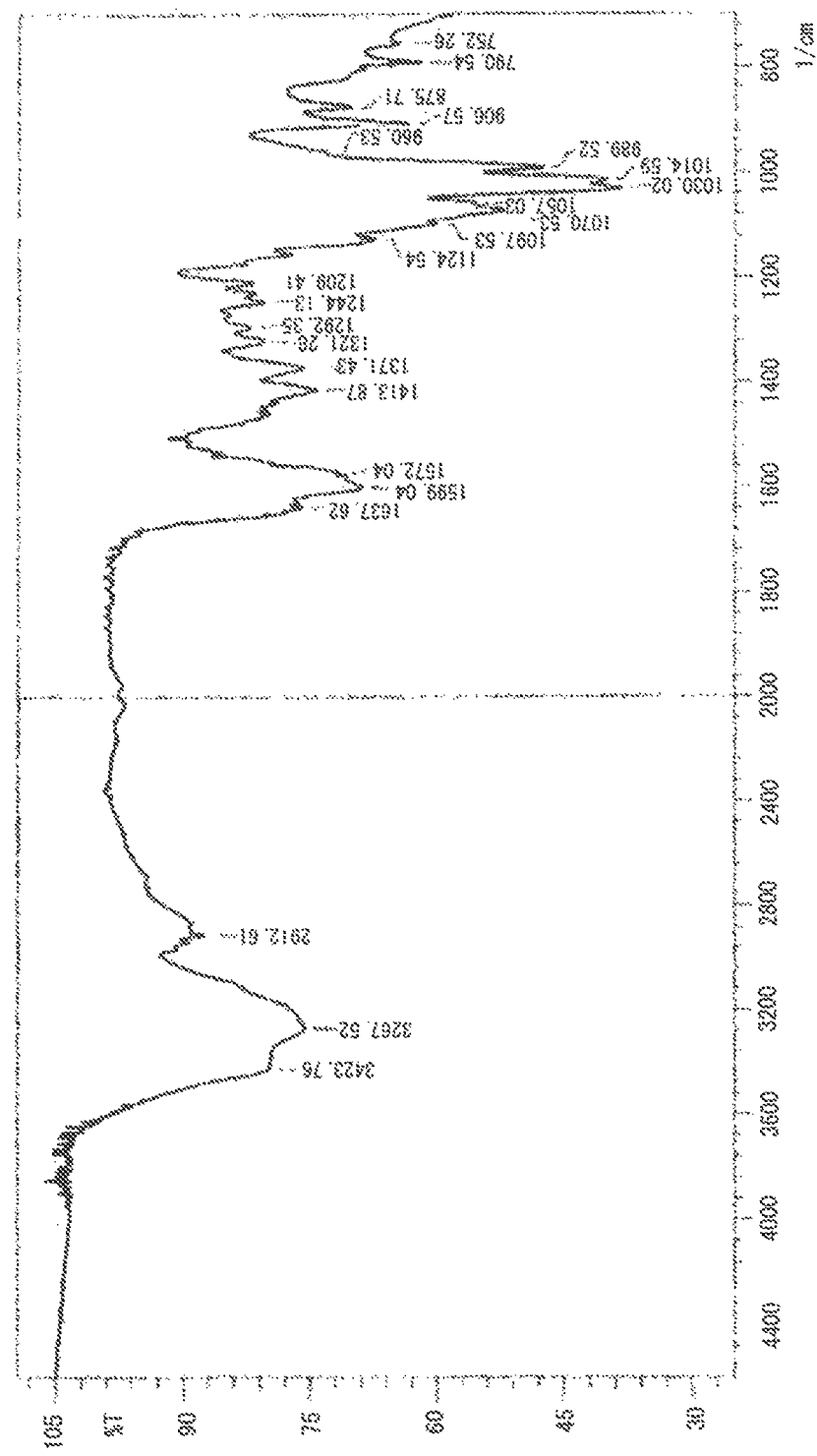
FIG. 3 illustrates the results of infrared spectroscopic (IR) analysis of the crystal of 6SL sodium salt 4.6-hydrate obtained in Example 2.

The crystal of 6SL sodium salt n-hydrate which can be produced by the above-mentioned production process may include, for example, a crystal of 6SL sodium salt 4,6-hydrate whose powder X-ray diffraction pattern using CuKα as the X-ray source is defined by the values shown in FIG. 2 and Table 2, a crystal of 6SL sodium salt 3,3-hydrate whose powder X-ray diffraction pattern is defined by the values shown in FIG. 5 and Table 5, a crystal of 6SL sodium salt 2,7-hydrate whose powder X-ray diffraction pattern is defined by the values shown in FIG. 7 and Table 8, a crystal of 6SL sodium salt 2,3-hydrate whose powder X-ray diffraction pattern is defined by the values shown in FIG. 8 and Table 9, and a crystal of 6SL sodium salt 4,6-hydrate which shows the infrared absorption spectrum illustrated in FIG. 3.

Further, the solvate crystal of 6SL sodium salt n-hydrate which can be produced by the above-mentioned production process may include, for example, 6SL sodium salt 2,5-hydrate 0.5-methanol solvate defined by the value shown in Table 7 in single crystal X-ray structure analysts.

2.3. Process for Producing Crystal of the Present Invention (3)

Also, the process for producing the crystal of the present invention may include a process for producing a crystal of 6SL sodium salt n-hydrate, comprising a step of dissolving N,N-dimethylformamide in a 6SL, aqueous solution containing a sodium-containing compound to precipitate a crystal of 6SL sodium salt n-hydrate in the aqueous solution, and a step of collecting the crystal of 6SL sodium salt n-hydrate from the aqueous solution.

The 6SL aqueous solution containing a sodium-containing compound may include the same examples as described in the above 2.1.

The method for dissolving N,N-dimethylformamide in a 6SL aqueous solution containing a sodium-containing compound to precipitate a crystal sodium salt n-hydrate in the aqueous solution may include, for example, a vapor diffusion method. The vapor diffusion method specifically includes a method in which the 6SL aqueous solution containing a sodium-containing compound is exposed to N,N-dimethylformamide vapor.

The temperature at which the 6SL aqueous solution containing a sodium-containing compound is exposed to N,N-dimethylformamide vapor may be any temperature as long as 6SL is not decomposed, but in order to decrease the degree of solubility and thereby enhance the crystallization rate of the crystal of 6SL sodium salt n-hydrate, the temperature may be generally 80° C. or less, preferably 70° C. or less, more preferably 60° C. or less, most preferably 50° C. or less. The lower limit of the temperature may be generally 0° C. or more, preferably 10° C. or more.

The time for which the 6SL aqueous solution containing a sodium-containing compound is exposed to N,N-dimethylformamide vapor can be generally from 3 days to 6 months, preferably from 14 days to 5 months, most preferably from 1 to 4 months.

The liquid amount of N,N-dimethylformamide to which the 6SL aqueous solution containing a sodium-containing compound is exposed in the above-mentioned method may be generally from 0.5 to 10 times, preferably from 1 to 9 times, most preferably from 2 to 8 times the amount of the aqueous solution.

The method for collecting the crystal of 6SL sodium salt n-hydrate from the aqueous solution may include the same method as described in the above 2.1 and 2.2.

Analysis Examples (1) Powder X-Ray Diffraction

The measurement was performed using a powder X-ray diffraction apparatus (XRD), Ultima IV (manufactured by Rigaku Corporation), according to the instruction book.

(2) Measurement of Concentration and Purity

The concentration and purity of 6SL were measured using the following HPLC analytical conditions.

Column: DionexCarboPac (trademark) PA1 BioLC (trademark), 4×250 mm

Guard column: DionexCarboPac (trademark) PA1 BioLC (trademark), 4×50 mm

Column temperature; 30° C.

Flow rate; 1 mL/min

Eluent: water/a 0.5 M sodium hydroxide aqueous solution/a 0.3 M sodium acetate aqueous solution (3) Measurement of Water Content of Crystal by Karl-Fisher Method The water content of the crystal was measured under the following conditions using an automatic water content measuring device AQV-2200 (manufactured by Hiranuma Sangyo Co., Ltd.) according to the instruction book.

Heating vaporization method, 110 to 171° C., 14 min (4) Measurement of Sodium Content The crystal of 6SL sodium salt was dissolved in 1 mol/L nitric acid, and the concentration of sodium ions contained in the crystal was measured using an atomic absorption spectrophotometer Z-2310 (manufactured by Hitachi High-Technologies Corporation) according to the instruction book.

(5) Measurement of Melting Point

The melting point was measured under the following conditions using Melting Point M-565 (manufactured by BUCHI Corporation) according to the instruction book.

140 to 200° C., 0.5° C./min (6) Infrared Spectroscopic (IR) Analysis

The measurement was performed using FTIR-8400 (manufactured by Shimadzu Corporation) according to the instruction book.

(7) Thermogravimetry-Differential Thermal Analysis (TG-DTA)

Weight change and differential thermal measurement was performed under the following conditions using EXSTAR 6000 (manufactured by Seiko Instruments, Inc.) according to the instruction book.

30 to 175° C., 0.5° C./min (8) Single Crystal X-Ray Structure Analysis

The analysis was performed using SuperNova (manufactured by Agilent Technologies Inc.) according to the instruction book.

Reference Example 1

Obtaining of Noncrystalline Amorphous 6SL Sodium Salt

Amorphous 6SL (200.5 g) was dissolved in water, and the pH was adjusted to 6.80 using a sodium hydroxide aqueous solution, whereby a 6SL sodium salt-containing aqueous solution (1000 mL) was prepared. A portion of this aqueous solution was freeze-dried, whereby a white powder was obtained. The powder X-ray diffraction of the powder was measured, and as a result, an X-ray diffraction peak was not confirmed. Therefore, the powder was found to be noncrystalline amorphous.

Reference Example 2

Study of Obtaining Crystal of 6SL Sodium Salt (1)

Crystallization of a 6SL sodium salt was tried with reference to Patent Document 2. Amorphous 6SL sodium salt (100 g) obtained in Reference Example 1 was dissolved in 250 mL of water, and the pH was adjusted to 9.0 using 1 mol/L NaOH. 17 mL of the obtained aqueous solution was used for the next step.

90% Ethanol (200 mL) was added to 8.0 g of a solid material obtained by concentrating (45° C., 15 hPa) 17 mL of the aqueous solution, followed by stirring for 24 hours, and then, a supernatant solution was removed, whereby a white solid material was obtained. The solid material did not show polarization with a polarised light microscope and therefore was confirmed to be noncrystalline amorphous, and thus, a crystal of 6SL sodium salt was not obtained.

Reference Example 2

Study of Obtaining Crystal of 6SL Sodium Salt (2)

Crystallization of 6SL sodium salt was tried with reference to Patent Document 3. Amorphous 6SL sodium salt (100 g) obtained in Reference Example 1 was dissolved in 250 mL of water, and the pH was adjusted to 9.0 using 1 mol/L NaOH. 17 mL of the obtained aqueous solution was used for the next step.

The aqueous solution (17 mL) was concentrated (50° C., 20 hPa), whereby a candy-like syrup was obtained. When 100 mL of 100% ethanol was added to the obtained syrup, a white precipitate was formed, and a suspension was obtained.

The precipitate was collected by filtration, washed twice with 50 mL of 100% ethanol, and then dried with forced air at 25° C. for 10 minutes, whereby 2.09 g of a precipitate was obtained. The obtained precipitate did not show polarization with a polarised light microscope and was confirmed to be noncrystalline amorphous.

96% Ethanol (70 mL) was added to 2.09 g of the precipitate, followed by stirring at 25° C. for 30 minutes to form a white suspension, and then, the suspension filtered, whereby 0.58 g of a candy-like solid material was obtained. The obtained candy-like solid material did not show polarization with a polarized light microscope and therefore was confirmed to be noncrystalline amorphous, and thus, a crystal of 6SL sodium salt was not obtained.

Reference Example 4

Study of Obtaining Crystal of 6SL Sodium Salt (3)

Crystallization of 6SL sodium salt was tried with reference to Patent Document 4. Amorphous 6SL sodium salt (100 g) obtained in Reference Example 1 was dissolved in 250 mL of water, and the pH was adjusted to 9.0 using 1 mol/L NaOH. 17 mL of the obtained aqueous solution was used for the next step.

When 200 mL of 100% methanol was added to 17 mL of the aqueous solution, a precipitate was not formed, and no change was observed in the solution. When the obtained suspension was concentrated (40° C., 100 hPa) to 20 mL a syrup-like solution was obtained, and a crystal was not obtained.

When the obtained syrup was further concentrated (50° C., 20 hPa) to dryness, 4.4 g of a white solid was obtained. The obtained precipitate did not show polarization with a polarized light microscope and therefore was confirmed to be noncrystalline amorphous, and thus, a crystal of 6SL sodium salt was not obtained.

Reference Example 5

Study of Obtaining Crystal of 6SL Sodium Salt (4)

Crystallization of 6SL sodium salt was tried with reference to Patent Document 4. Amorphous 6SL sodium salt (100 g) obtained in Reference Example 1 was dissolved in 250 mL of water, and the pH was adjusted to 9.0 using 1 mol/L NaOH. 17 mL of the obtained aqueous solution was used for the next step.

When 200 mL of 100% ethanol was added to 17 mL of the aqueous solution a white precipitate was formed, and a suspension was obtained. After the obtained suspension was concentrated to 100 mL, the precipitate was collected by filtration and dried with forced air at 25° C., whereby 6.3 g of a precipitate was obtained. The obtained precipitate did not show polarization with a polarized light microscope and therefore was confirmed to be noncrystalline amorphous, and thus, a crystal of 6SL sodium salt was not obtained.

Reference Example 6

Study of Obtaining Crystal of 6SL Sodium Salt (5)

Crystallization of 6SL sodium salt was tried with reference to Patent Document 4. Amorphous 6SL sodium salt (100 g) obtained in Reference Example 1 was dissolved in 250 mL of water, and the pH was adjusted to 9.0 using 1 mol/L NaOH. 17 mL of the obtained aqueous solution was used for the next step.

When 200 mL of 100% isopropanol was added to 17 mL of the aqueous solution, a white precipitate was formed, and a suspension was obtained. After the obtained suspension was concentrated to 100 mL, the precipitate was collected by filtration, and dried with forced air at 25° C., whereby 4.9 g of a precipitate was obtained. The obtained precipitate did not show polarisation with a polarized light microscope and therefore was continued to be noncrystalline amorphous, and thus, a crystal of 6SL sodium salt was not obtained.

EXAMPLES

Examples are described below, but the present invention is not limited to the following Examples.

Example 1

Obtaining Crystal of 6SL Sodium Salt n-Hydrate (1)

After 6.10 g of amorphous 6SL sodium salt obtained in Reference Example 1 was suspended in 100 mL of 100% methanol for 10 minutes, the resulting suspension was filtered, whereby 95 mL of a filtrate was obtained. 30 mL of the obtained filtrate was used for the next step.

The filtrate (30 mL) was stirred at 25° C. for 12 hours thereby a crystal was naturally crystallized. After the crystal slurry was further matured for 12 hours, the crystal was collected by filtration, and dried with forced air at 25° C., whereby 550 mg of a crystal was obtained.

The results of powder X-ray diffraction of the crystal are shown in Table 1. In the Table, "2θ" indicates the diffraction angle (2θ), and "Relative Intensity" indicates the relative intensity ratio ($I/I_0$). The results when the relative intensity ratio was 5 or more are shown.

TABLE 1

| 2θ | Relative Intensity |
|---|---|
| 6.5 | 90 |
| 8.1 | 24 |
| 10.0 | 26 |
| 12.2 | 36 |
| 13.1 | 60 |
| 14.3 | 52 |
| 15.0 | 51 |
| 16.4 | 80 |
| 17.2 | 83 |
| 17.6 | 100 |
| 18.4 | 85 |
| 19.9 | 92 |
| 20.8 | 92 |
| 21.6 | 80 |
| 23.6 | 95 |
| 24.2 | 69 |
| 25.7 | 76 |
| 26.5 | 46 |
| 28.8 | 54 |
| 29.2 | 43 |
| 30.5 | 55 |
| 31.6 | 37 |
| 34.9 | 39 |
| 35.5 | 37 |
| 37.3 | 45 |
| 38.1 | 37 |

The amount of water contained in the crystal was measured by the Karl-Fisher method, and as a result, it was 9.3 wt %, and the crystal 6SL sodium salt was found to be 6SL sodium sale 4.0-hydrate by comparison with the theoretical amount of water.

Example 2

Obtaining Crystal of 6SL Sodium Salt n-Hydrate (2)

Amorphous 6SL (225.1 g in terms of free form) was dissolved in water, and the pH was adjusted to 6.81 using a sodium hydroxide aqueous solution, and the volume was made up to 1.166 mL. This aqueous solution was concentrated to 323 mL, and 81 mL of the obtained concentrated solution was used for the next step.

While maintaining 81 mL of the concentrated solution at 25° C., 3.0 g of the crystal obtained in Example 1 was added thereto as a seed crystal. Thereto, 700 mL of 95% methanol was added dropwise over 4 hours, whereby a crystal was precipitated. After the crystal slurry was matured for 12 hours, the crystal was collected by filtration, and washed with a 95% methanol aqueous solution, and then dried with forced air at 25° C., whereby 61.2 g of a crystal was obtained.

In the measurement of purity by HPLC, it was confirmed that a crystal of 6SL having a purity of 99.6% (area %) or more was obtained, and by repeating the above-mentioned crystallization operation by dissolving the crystal in water again, a crystal of 6SL having a purity of 99.8% (area %) or more could be obtained.

The results of powder X-ray diffraction of the crystal are shown in Table 2. In the Table, "2θ" indicates the diffraction angle (2θ°), and "Relative Intensity" indicates the relative intensity ratio ($I/I_0$). The results when the relative intensity ratio was 5 or more are shown.

TABLE 2

| 2θ | Relative Intensity |
|---|---|
| 6.7 | 100 |
| 7.6 | 5 |
| 8.3 | 6 |
| 10.0 | 5 |
| 11.0 | 6 |
| 11.6 | 5 |
| 12.4 | 7 |
| 12.8 | 7 |
| 13.3 | 38 |
| 13.6 | 7 |
| 14.3 | 14 |
| 15.1 | 12 |
| 16.3 | 11 |
| 16.5 | 20 |
| 17.3 | 18 |
| 17.7 | 25 |
| 18.5 | 26 |
| 20.0 | 34 |
| 20.7 | 10 |
| 20.9 | 13 |
| 21.1 | 13 |
| 21.3 | 19 |
| 21.8 | 24 |
| 22.2 | 8 |
| 22.8 | 7 |
| 23.7 | 21 |
| 23.9 | 18 |
| 24.0 | 16 |
| 24.4 | 15 |
| 24.8 | 8 |
| 25.2 | 9 |
| 25.7 | 18 |
| 25.9 | 12 |
| 26.7 | 17 |
| 28.8 | 19 |
| 29.3 | 10 |
| 29.9 | 7 |
| 30.5 | 12 |
| 30.8 | 9 |
| 31.8 | 13 |
| 33.2 | 7 |
| 33.9 | 7 |
| 35.0 | 11 |
| 35.4 | 7 |
| 36.0 | 7 |
| 37.4 | 9 |
| 38.1 | 8 |
| 38.7 | 7 |

The sodium content of the crystal was measured by atomic absorption spectrophotometry, and as a result. It was 3.66 wt % and substantially coincided with the theoretical value (3.50 wt %) of a monosodium salt.

In addition, the amount of water contained in the crystal was measured by the Karl-Fisher method, and as a result, it was 10.2 wt %, and the crystal of 6SL sodium salt was found to be 6SL sodium salt 4.6-hydrate by comparison with the theoretical amount of water.

Various physical properties of the crystal obtained in the Example 2 are shown in Table 3. As for the pH, an aqueous solution at 100 g/L in terms of crystal of 6SL sodium salt 4.6-hydrate was measured.

TABLE 3

| Water Content % | Sodium Content % | Melting Point ° C. | pH |
|---|---|---|---|
| 10.2 | 3.66 | 179.9 | 6.23 |

As shown in table 3, the melting point of the crystal of 6SL sodium salt 4.6-hydrate is 179.9° C. which is higher than the melting point of around 160° C. of known amorphous 6SL sodium salt. Therefore, it was revealed that the crystal of 6SL sodium salt 4.6-hydrate is stable under high temperature conditions.

Further, with respect to the crystal of 6SL sodium salt 4.6-hydrate and known amorphous 6SL sodium salt, the degree of coloration when a heat load at 60° C. was applied was compared, and the results are shown in Table 4.

The degree of coloration is expressed by transmittance T % 430 nm $100 \times 10^{-A}$ (A=Abs: 430 nm, 1 cm), which was obtained by dissolving each substance at 100 g/L in terms of an anhydrate and performing measurement for the solution.

TABLE 4

| Elapsed Time [days] | 0 | 3 | 6 |
|---|---|---|---|
| Crystal of sodium salt | 99.9 | 99.8 | 99.8 |
| Amorphous salt | 99.4 | 99.0 | 98.8 |

As shown in Table 4, the degree of coloration during storage of the crystal of 6SL sodium salt 4.6-hydrate was lower than that of known amorphous 6SL sodium salt. Therefore, it was found that the crystal of 6SL sodium salt 4.6-hydrate has higher storage stability than known amorphous 6SL sodium salt.

The hygroscopicity of the obtained crystal of 6SL sodium salt 4.6-hydrate and that of a 6SL sodium reagent (amorphous salt, manufactured by Carbosynth Limited) were compared under the following conditions.

Storage condition: 30° C., relative humidity: 80% (apparatus: THE051FA, manufactured by Advantec Toyo Kaisha Ltd.).

Measurement method: After about 100 mg of a sample was weighed with a precision balance, the sample was packed in a glass container and stored under the above-mentioned conditions. Thereafter, the sample was weighed again, and the weight change ratio was calculated.

The results are shown in Table 5. Incidentally, the weight of the sample at each elapsed time was measured by assuming the weight of each sample at the start of the test to be 100%.

TABLE 5

| Elapsed Time [hours] | 0 | 0.5 | 2.5 | 8 | 20 |
|---|---|---|---|---|---|
| Weight of crystal (%) | 100.0 | 98.8 | 98.6 | 98.4 | 98.7 |
| Weight of amorphous salt (%) | 100.0 | 114.4 | 119.6 | 122.9 | 124.1 |

As shown in Table 5, the obtained crystal of 6SL sodium salt 4.6-hydrate had lower hygroscopicity than the amorphous salt, and therefore was confirmed to have higher storage stability than the amorphous salt.

Example 3

Obtaining Crystal of 6SL Sodium Salt n-Hydrate (3)

The crystal of 6SL sodium salt 4.6-hydrate (12.0 g) obtained in Example 2 was dried at room temperature for 21 hours using a vacuum dryer, whereby 11.6 g of a crystal was obtained.

The amount of water contained in the crystal was measured by the Karl-Fisher method, and as a result, it was 8.3 wt %, and the crystal of 6SL sodium salt was found to be 6SL sodium salt 3.3-hydrate by comparison with the theoretical amount of water.

In addition, the results of powder X-ray diffraction of the crystal are shown in Table 6. In the Table, "2θ" indicates the diffraction angle (2θ°), and "Relative Intensity" indicates the relative intensity ratio ($I/I_0$). The results when the relative intensity ratio was 5 or more are shown.

TABLE 6

| 2θ | Relative Intensity |
|---|---|
| 6.8 | 100 |
| 7.6 | 6 |
| 8.3 | 7 |
| 10.1 | 6 |
| 11.0 | 8 |
| 11.6 | 6 |
| 12.3 | 9 |
| 12.9 | 10 |
| 13.4 | 40 |
| 14.3 | 19 |
| 15.2 | 13 |
| 16.5 | 26 |
| 17.3 | 20 |
| 17.8 | 31 |
| 18.5 | 29 |
| 20.1 | 42 |
| 21.0 | 18 |
| 21.4 | 24 |
| 21.8 | 27 |
| 22.2 | 12 |
| 22.8 | 9 |
| 23.7 | 28 |
| 24.1 | 23 |
| 24.4 | 19 |
| 24.9 | 10 |
| 25.3 | 13 |
| 25.8 | 24 |
| 26.1 | 14 |
| 26.8 | 21 |
| 28.9 | 24 |
| 29.4 | 13 |
| 30.5 | 16 |
| 30.9 | 13 |
| 31.9 | 15 |
| 33.9 | 9 |
| 35.1 | 13 |
| 36.1 | 9 |
| 37.3 | 12 |
| 38.2 | 10 |
| 38.8 | 9 |

As shown in Table 6, the results of the crystal substantially coincided with the results of powder X-ray diffraction of the crystals obtained in Examples 1 and 2. Therefore, it was found that the same crystal structure with a different hydration number (n) exists in the crystal of 6SL sodium salt n-hydrate.

Figure 4:
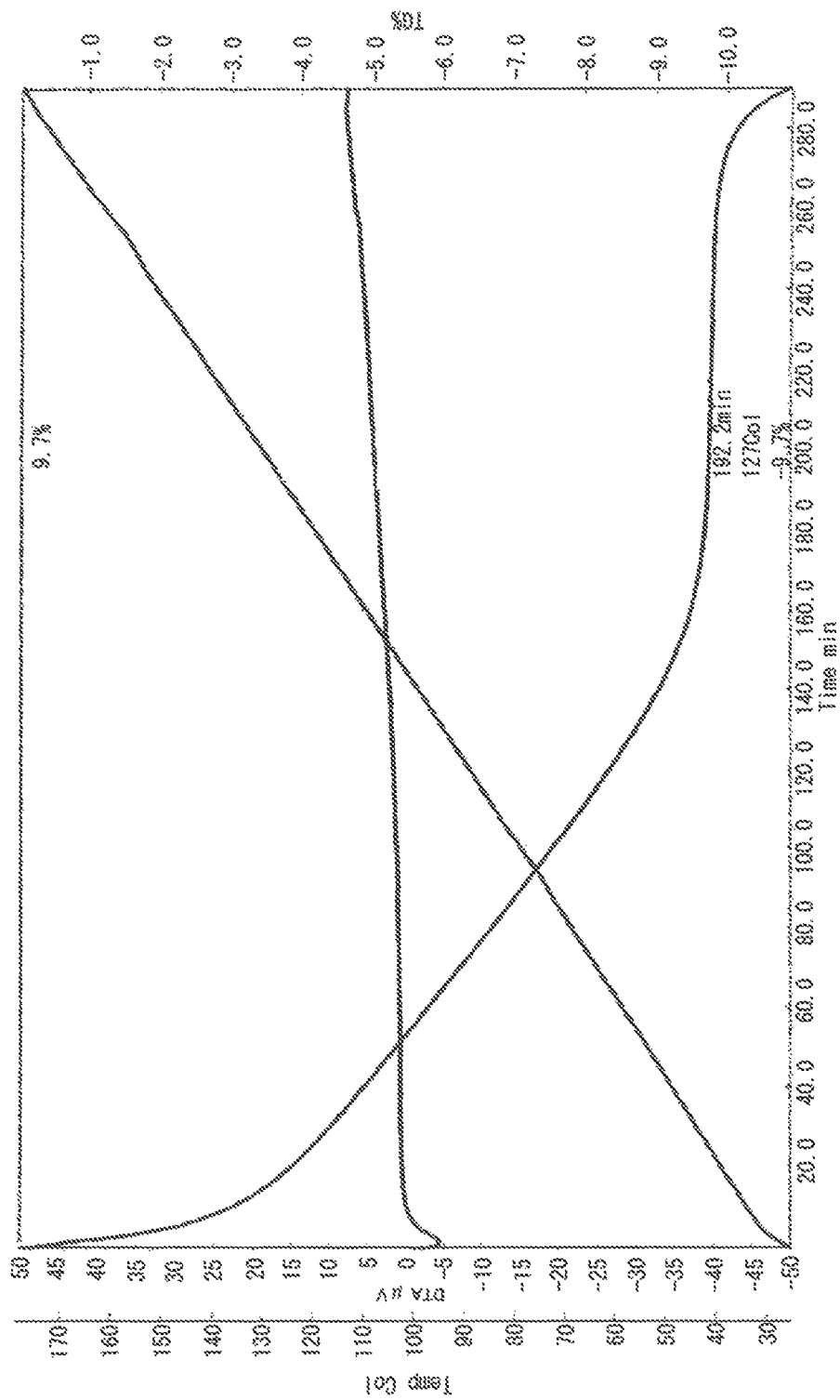
FIG. 4 illustrates the results of thermogravimetry-differential thermal analysis (TG-DTA) of a crystal of 6SL sodium salt 4.6-hydrate obtained in Example 3.

Further, from the results of thermogravimetry-differential thermal analysis of the 4.6-hydrate obtained in Example 2 (FIG. 4), the water molecules of the 4.6-hydrate were gradually dehydrated as the temperature was increased (30° C. to 127° C.), and the 4.6-hydrate was converted into an anhydrate (n=0) at 127° C., and further, crystal transition accompanied by heat absorption or heat generation was not observed during the process, and therefore, it was revealed that crystal states of an n-hydrate continuously ranging from an anhydrate to a 5.0-hydrate exist in the crystal of 6SL sodium salt n-hydrate.

Example 4

Obtaining Crystal of 6SL Sodium Salt 2.5-Hydrate 0.5-Methanol Solvate

Amorphous 6SL sodium salt (100 g) obtained in Reference Example 1 was dissolved in 300 mL of water, and the resulting solution was concentrated (50° C., 15 hPa) to a volume of 150 mL.

To the obtained concentrated solution, 83 mL of 100% methanol was added at 2° C. over 2 hours, and thereafter, 1.0 g of the crystal of 6SL sodium salt 4.6-hydrate obtained in f Example 2 was added thereto as a seed crystal, and a crystal was precipitated.

Further, 259 mL of 100% methanol was added at 25° C. over 12 hours, followed by maturation at 40° C. for 3 days to grow the crystal of 6SL sodium salt, whereby a slurry was obtained.

In order to determine the structure of the precipitated crystal, the precipitated crystal of 6SL sodium salt was selected to single crystal X-ray diffraction (SXRD) using a measuring device (a single crystal X-ray structure analyzer R-AXIS RAPID, manufactured by Rigaku Corporations).

First a single crystal of 6SL sodium salt was placed on a diffractometer, and a diffraction image was measured using an X-ray with a predetermined wavelength in the air at room temperature or in an inert gas stream at a predetermined temperature.

Subsequently, from a set of a plane index calculated from the diffraction image and a diffraction intensity, structure determination by a direct method and structure refinement [Acta Cryst, A64, 112 (2008)] by a least-squares method were performed, whereby a single crystal structure was obtained. The results are summarized in table 7.

TABLE 7

| Crystal data | |
|---|---|
| Chemical Formula | $[Na^+ \cdot (C_{23}H_{38}NO_{19})]_2 \cdot 5H_2O \cdot CH_3OH$ |
| $M_r$ | 1433.19 |
| Crystal System, space group | Triclinic, P1 |
| Temperature (K) | 100 |
| a, b, c (Å) | 9.0695(7), 12.4146(8), 14.6177(11) |
| α, β, γ (°) | 71.326(6), 79.972(6), 89.591(6) |
| V (Å$^3$) | 1533.3(2) |
| Z | 1 |
| Radiation type | Cu Kα |
| μ (mm$^{-1}$) | 1.33 |
| Crystal size (mm) | 0.20 × 0.02 × 0.01 |
| Data collection | |
| Diffractometer | Agilent SuperNova |
| Absorption correction | Multi-scan |
| No. of measured, independent and observed [I > σ(I)] reflections | 25475, 11106, 6556 |
| $R_{int}$ | 0.1680 |
| (sin θ/λ)$_{max}$ (Å$^{-1}$) | 0.623 |
| Refinement | |
| $R[F^2 > 2σ(F^2)]$, $wR(F^2)$, S | 0.1014, 0.2948, 1.111 |
| No. of reflections | 11106 |
| No. of parameters | 902 |
| H-atom treatment | H-atom parameters constrained |
| $Δρ_{max}$, $Δρ_{min}$ (eÅ$^{-3}$) | 0.76, −0.50 |

TABLE 7-continued

| | |
|---|---|
| Absolute structure | Flack x determined using 5027 Friedel pairs (Flack, 1983) |
| Absolute structure parameter | 0.1(2) |

Computer programs: CrysAlisPro (Rigaku, 2015), CrystalStructure (Rigaku, 2015), Superflip (Palatinus & Chapuis, 2007), SHELXL-97 (Sheldrick, 2008), Mercury (Macrae et al. 2008).
References
Flack, H. D. (1983). Acta Cryst. A39. 876-881.
Macrae, C.F., Bruno, I.J., Chisholm, J.A., Edgington, P.R., McCabe. P., Pidcock, E., Rodrigues-Monge, L., Taylor, R., van de Streek, J., Wood, P. A. (2008). J. Appl. Cryst. 41, 466-470.
Sheldrick, G.M. (2008). Acta Cryst. A64, 112-122.
Palatinus L., Chapuis G. (2007), J. Appl. Cryst. 40, 786-790.

As shown in Table 7, as a result of the above-mentioned measurement, it was confirmed that the crystal of 6SL sodium salt, and is a 2.5-hydrate 0.5-methanol solvate having a water molecule and a methanol molecule within a unit cell.

Figure 6:
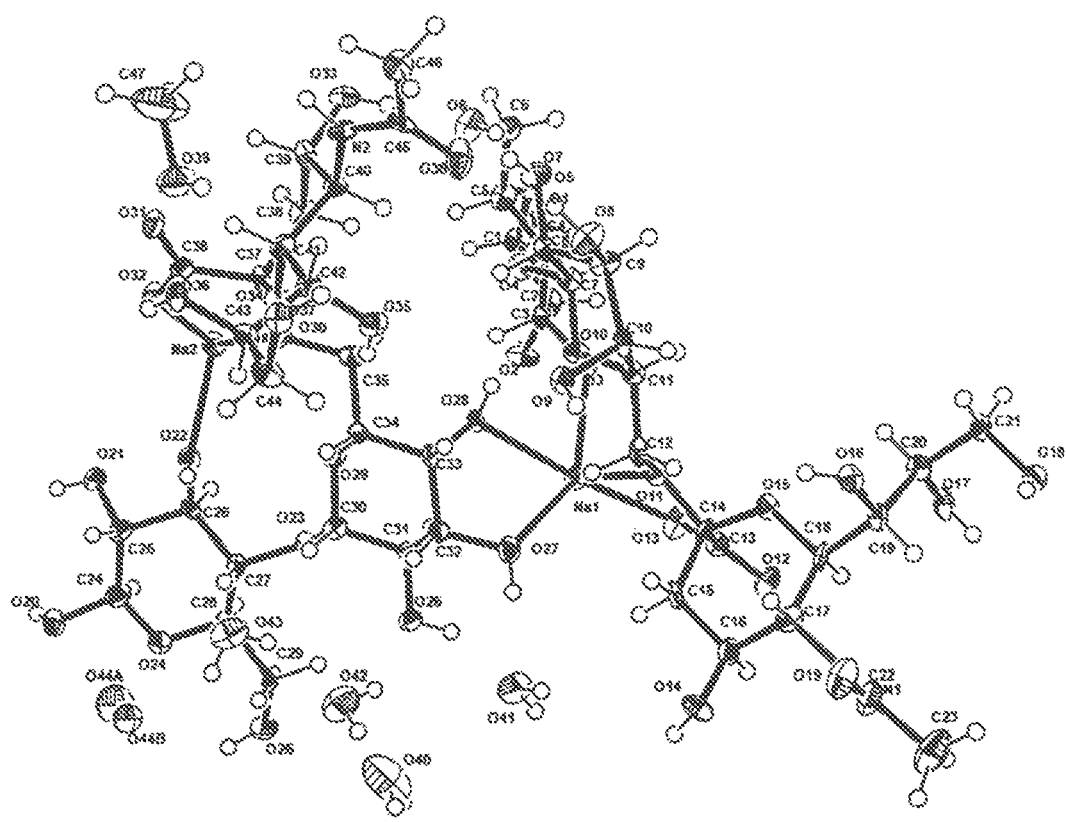
FIG. 6 illustrates an ORTEP diagram of a crystal of 6SL sodium salt 2.5-hydrate 0.5-methanol solvate obtained in Example 4 by single crystal X-ray structure analysis.

The ORTEP diagram of the crystal of 6SL sodium salt 2.5-hydrate 0.5-methanol solvate obtained as a result of the single crystal X-ray structure analysis is shown in FIG. 6.

Example 5

Obtaining Crystal of 6SL Sodium Salt n-Hydrate (4)

The crystal of 6SL sodium salt 2.5-hydrate 0.5-methanol solvate was collected by filtration through centrifugation of the crystal slurry obtained Example 4, whereby 137.9 g of a crystal was obtained. The crystal was further vacuum-dried (35° C., 50 hPa, 24 hours), whereby 73.9 g of a crystal was obtained.

The results of powder X-ray diffraction of the crystal are shown in FIG. 7 and Table 8. In the Table, "2θ" indicates the diffraction angle (2θ°), and "Relative Intensity" indicates the relative intensity ratio ($I/I_0$). The results when the relative intensity ratio was 5 or more are shown.

TABLE 8

| 2θ | Relative Intensity |
|---|---|
| 6.10 | 18 |
| 6.86 | 100 |
| 13.46 | 29 |
| 14.34 | 7 |
| 15.20 | 5 |
| 16.60 | 8 |
| 17.38 | 9 |
| 17.82 | 10 |
| 18.58 | 9 |
| 20.12 | 16 |
| 20.84 | 8 |
| 21.48 | 13 |
| 21.90 | 11 |
| 23.76 | 13 |
| 24.04 | 13 |
| 24.16 | 12 |
| 25.62 | 10 |
| 26.88 | 14 |
| 29.00 | 14 |
| 30.52 | 8 |
| 31.92 | 10 |
| 35.14 | 8 |

Further, the amount of methanol contained in the crystal was measured by gas chromatography, and as a result, it was 0.39 wt %, and it was confirmed that methanol was released from the crystal cell of the 6SL sodium salt 2.5-hydrate 0.5-methanol solvate.

In addition, the amount of water contained in the crystal was measured by the Karl-Fisher method, and as a result, it was 6.3 wt %, and the crystal of 6SL sodium salt was found to be 6SL sodium salt 2.7-hydrate by comparison with the theoretical amount of water.

When the chart diagram in FIG. 7 and the chart diagram of the crystal obtained in Example 7 were compared, these coincided well with each other. Therefore, the crystal was confirmed to have the same crystal form as that of the crystal obtained in Example 2.

Example 6

Obtaining Crystal of 6SL Sodium Salt n-Hydrate (5)

Amorphous 6SL sodium salt (100 g) obtained in Reference Example 1 was dissolved in 300 mL of water, and the resulting solution was concentrated (50° C., 15 hPa) to a volume of 105 mL. 1 mL of the obtained concentrated solution was used for the next step.

The aqueous solution (1 mL) was packed in a 5-mL glass sample bottle, and stored by being left to stand in a 50-mL, glass sample bottle packed with about 5 mL of N,N-dimethylformamide (hereinafter referred to as DMF) so that the aqueous solution was exposed to the DMF vapor at room temperature for 3 months. As a result, a needle-like crystal was precipitated from the aqueous solution.

Example 7

Obtaining Crystal of 6SL Sodium Salt n-Hydrate (6)

Amorphous 6SL sodium salt (10 g) obtained in Reference Example 1 was dissolved in water, and the volume was made up to 20 mL. 1 mL of the obtained concentrated solution was used for the next step.

After 20 mL of DMF was added to 1 mL of the aqueous solution at room temperature over 1 hour, about 10 mg of the needle-like crystal obtained in Example 6 was added thereto. As a result, a crystal was precipitated. The crystal was collected by filtration, and dried with forced air 25° C., whereby 70 mg of a crystal was obtained.

The results of powder X-ray diffraction of the crystal are shown in FIG. 8 and Table 9. In the Table, "2θ" indicates the diffraction angle (2θ°), and "Relative Intensity" indicates the relative intensity ratio $I/I_0$).

TABLE 9

| 2θ | Relative Intensity |
|---|---|
| 5.86 | 100 |
| 11.74 | 14 |
| 12.66 | 2 |
| 14.52 | 4 |
| 14.94 | 3 |
| 15.26 | 3 |
| 16.12 | 2 |
| 17.42 | 4 |
| 17.82 | 5 |
| 18.88 | 3 |
| 19.68 | 4 |
| 20.08 | 8 |
| 21.00 | 6 |
| 22.14 | 3 |
| 23.64 | 6 |
| 24.64 | 4 |
| 26.40 | 2 |
| 28.30 | 3 |
| 31.48 | 3 |

When the purity of the crystal was measured, it was 98.8%, and it was found that the crystal is surely a crystal of 6SL sodium salt. In addition, the amount of water contained in the crystal was measured by the Karl-Fisher method, and as a result, it was 5.3 wt %, and the crystal of 6SL sodium salt was found to be 6SL sodium salt 2.3-hydrate by comparison with the theoretical amount of water.

When the chart diagram in FIG. 8 and the chart diagrams of the crystal obtained in Example 2 were compared, these did not coincide with each other. Therefore, the crystal was confirmed to have a crystal form different from that of the crystal obtained in Example 2.

The melting point of the crystal was measured, and as a result, it was 169.9° C.

While the present invention has been described in detail with reference to specific embodiments, it is apparent to those skilled in the art that various changes and modification can be made without departing from the spirit and scope of the present invention. The preset application is based on Japanese Patent Application (Japanese Patent Application No. 2015-225652) filed on Nov. 18, 2015 and the entire contents of which are incorporated herein by reference. Further, all references cited herein are incorporated herein by reference in their entirety.

INDUSTRIAL APPLICABILITY

According to the present invention, a crystal of 6SL sodium salt, which is useful, for example, as a product, a raw material, an intermediate, or the like of health food, pharmaceuticals, cosmetics, and the like, and a production process of the crystal are provided.

The invention claimed is:

1. A crystal of 6'-sialyllactose (6SL) sodium salt.

2. The crystal according to claim 1, wherein the crystal is a crystal of 6SL sodium salt n-hydrate, wherein (n represents an arbitrary number of 0 to 5, and when n is 0, the crystal is 6SL sodium salt) anhydrate.

3. The crystal according to claim 2, wherein the crystal of 6SL sodium salt n-hydrate is a crystal of 6SL sodium salt n-hydrate described in any one of the following (i) to (iii):
  (i) a crystal of 6SL sodium salt n-hydrate which has peaks at diffraction angles (2θ) of 6.7±0.2°, 13.3±0.2°, 17.7±0.2°, 18.5±0.2°, and 20.0±0.2° in powder X-ray diffraction;
  (ii) a crystal of 6SL sodium salt n-hydrate which further has peaks at diffraction angles (2θ) of 16.5±0.2°, 21.3±0.2°, 21.8±0.2°, 23.6±0.2°, and 28.8±0.2° in addition to the peaks at the diffraction angles (2θ) described in (i) in powder X-ray diffraction; and
  (iii) a crystal of 6SL sodium salt n-hydrate which further has peaks at diffraction angles (2θ) of 17.3±0.2°, 23.9±0.2°, 24.0±0.2°, 25.7±0.2°, and 26.7±0.2° in addition to the peaks at the diffraction angles (2θ) described in (i) and (ii) in powder X-ray diffraction.

4. A process for producing a crystal of 6SL sodium salt n-hydrate or a solvate crystal of 6SL sodium salt n-hydrate, wherein n represents an arbitrary number of 0 to 5, and when n is 0, the crystal of 6SL sodium salt n-hydrate is 6SL sodium salt anhydrate, comprising a step of dissolving amorphous 6SL sodium salt in methanol solution, a step of precipitating a crystal of 6SL sodium salt n-hydrate or a solvate crystal of 6SL sodium salt n-hydrate by leaving the solution to stand or stirring the solution, and a step of collecting the crystal of 6SL sodium salt n-hydrate or the solvate crystal of 6SL sodium salt n-hydrate from the solution, wherein the crystal of 6SL sodium salt n-hydrate is a crystal of 6SL sodium salt n-hydrate described in any one of the following (i) to (iii):
  (i) a crystal of 6SL sodium salt n-hydrate which has peaks at diffraction angles (2θ) of 6.7±0.2°, 13.3±0.2°, 17.7±0.2°, 18.5±0.2°, and 20.0±0.2° in powder X-ray diffraction;
  (ii) a crystal of 6SL sodium salt n-hydrate which further has peaks at diffraction angles (2θ) of 16.5±0.2°, 21.3±0.2°, 21.8±0.2°, 23.6±0.2°, and 28.8±0.2° in addition to the peaks at the diffraction angles (2θ) described in (i) in powder X-ray diffraction; and
  (iii) a crystal of 6SL sodium salt n-hydrate which further has peaks at diffraction angles (2θ) of 17.3±0.2°, 23.9±0.2°, 24.0±0.2°, 25.7±0.2°, and 26.7±0.2° in addition to the peaks at the diffraction angles (2θ) described in (i) and (ii) in powder X-ray diffraction.

5. A process for producing a crystal of 6SL sodium salt n-hydrate or a solvate crystal of 6SL sodium salt n-hydrate, wherein n represents an arbitrary number of 0 to 5, and when n is 0, the crystal of 6SL sodium salt n-hydrate is 6SL sodium salt anhydrate, comprising a step of adding a crystal of 6SL sodium salt n-hydrate as a seed crystal to a 6SL aqueous solution containing sodium hydroxide or a carbonate, sulfate, nitrate, or chloride of sodium, a step of precipitating a crystal of 6SL sodium salt n-hydrate or a solvate crystal of 6SL sodium salt n-hydrate in the aqueous solution, and a step of collecting the crystal of 6SL sodium salt n-hydrate or the solvate crystal of 6SL sodium salt n-hydrate from the aqueous solution, wherein the crystal of 6SL sodium salt n-hydrate is a crystal of 6SL sodium salt n-hydrate described in any one of the following (i) to (iii):
  (i) a crystal of 6SL sodium salt n-hydrate which has peaks at diffraction angles (2θ) of 6.7±0.2°, 13.3±0.2°, 17.7±0.2°, 18.5±0.2°, and 20.0±0.2° in powder X-ray diffraction;
  (ii) a crystal of 6SL sodium salt n-hydrate which further has peaks at diffraction angles (2θ) of 16.5±0.2°, 21.3±0.2°, 21.8±0.2°, 23.6±0.2°, and 28.8±0.2° in addition to the peaks at the diffraction angles (2θ) described in (i) in powder X-ray diffraction; and
  (iii) a crystal of 6SL sodium salt n-hydrate which further has peaks at diffraction angles (2θ) of 17.3±0.2°, 23.9±0.2°, 24.0±0.2°, 25.7±0.2°, and 26.7±0.2° in addition to the peaks at the diffraction angles (2θ) described in (i) and (ii) in powder X-ray diffraction.

6. The production process according to claim 5, wherein the step of precipitating a crystal of 6SL sodium salt n-hydrate or a solvate crystal of 6SL sodium salt n-hydrate in the aqueous solution is a step of precipitating the crystal of 6SL sodium salt n-hydrate or the solvate crystal of 6SL sodium salt n-hydrate by adding or adding dropwise methanol solution to the aqueous solution, wherein the crystal of 6SL sodium salt n-hydrate is a crystal of 6SL sodium salt n-hydrate described in any one of the following (i) to (iii):
  (i) a crystal of 6SL sodium salt n-hydrate which has peaks at dull action angles (2θ) of 6.7±0.2°, 13.3±0.2°, 17.7±0.2°, 18.5±0.2°, and 20.0±0.2° in powder X-ray diffraction;
  (ii) a crystal of 6SL sodium salt n-hydrate which further has peaks at diffraction angles (2θ) of 16.5±0.2°, 21.3±0.2°, 21.8±0.2°, 23.6±0.2°, and 28.8±0.2° in addition to the peaks at the diffraction angles (2θ) described in (i) in powder X-ray diffraction; and
  (iii) a crystal of 6SL sodium salt n-hydrate which further has peaks at diffraction angles (2θ) of 17.3±0.2°, 23.9±0.2°, 24.0±0.2°, 25.7±0.2°, and 26.7±0.2° in addition to the peaks at the diffraction angles (2θ) described in (i) and (ii) in powder X-ray diffraction.

7. The production process according to claim 4, further comprising a step of drying the crystal of 6SL sodium salt n-hydrate or the solvate crystal of 6SL sodium salt n-hydrate.

8. The production process according to claim 5, further comprising a step of drying the crystal of 6SL sodium salt n-hydrate or the solvate crystal of 6SL sodium salt n-hydrate.

9. The production process according to claim 6, further comprising a step of drying the crystal of 6SL sodium salt n-hydrate or the solvate crystal of 6SL sodium salt n-hydrate.

10. The production process according to claim 4, wherein the solvate crystal of 6SL sodium salt n-hydrate is a crystal of 6SL sodium salt 2.5-hydrate 0.5-methanol solvate.

11. The production process according to claim 6, wherein the solvate crystal of 6SL sodium salt n-hydrate is a crystal of 6SL sodium salt 2.5-hydrate 0.5-methanol solvate.

12. The production process according to claim 7, wherein the solvate crystal of 6SL sodium salt n-hydrate is a crystal of 6SL sodium salt 2.5-hydrate 0.5-methanol solvate.

13. The production process according to claim 9, wherein the solvate crystal of 6SL sodium salt n-hydrate is a crystal of 6SL sodium salt 2.5-hydrate 0.5-methanol solvate.

14. The crystal according to claim 2, wherein the crystal of 6SL sodium salt n-hydrate is a crystal of 6SL sodium salt n-hydrate described in any one of the following (iv) to (vi):
(iv) a crystal of 6SL sodium salt n-hydrate which has peaks at diffraction angles (2θ) of 5.9±0.2°, 11.7±0.2°, 20.1±0.2°, 21.0±0.2°, and 23.6±0.2° in powder X-ray diffraction;
(v) a crystal of 6SL sodium salt n-hydrate which further has peaks at diffraction angles (2θ) of 17.8±0.2°, 14.5±0.2°, 17.4±0.2°, 19.7±0.2°, and 24.6±0.2° in addition to the peaks at the diffraction angles (2θ) described in (iv) in powder X-ray diffraction; and
(vi) a crystal of 6SL sodium salt n-hydrate which further has peaks at diffraction angles (2θ) of 14.9±0.2°, 18.9±0.2°, 22.1±0.2°, 28.3±0.2°, and 31.5±0.2° in addition to the peaks at the diffraction angles (2θ) described in (iv) and (v) in powder X-ray diffraction.

15. A process for producing a crystal of 6SL sodium salt n-hydrate, wherein n represents an arbitrary number of 0 to 5, and when n is 0, the crystal of 6SL sodium salt n-hydrate is 6SL sodium salt anhydrate, comprising a step of dissolving N,N-dimethylformamide in a 6SL aqueous solution containing sodium hydroxide or a carbonate, sulfate, nitrate, or chloride of sodium to precipitate a crystal of 6SL sodium salt n-hydrate in the aqueous solution, and a step of collecting the crystal of 6SL sodium salt n-hydrate from the aqueous solution, wherein the crystal of 6SL sodium salt n-hydrate is a crystal of 6SL sodium salt n-hydrate described in any one of the following (iv) to (vi):
(iv) a crystal of 6SL sodium salt n-hydrate which has peaks at diffraction angles (2θ) of 5.9±0.2°, 11.7±0.2°, 20.1±0.2°, 21.0±0.2°, and 23.6±0.2° in powder X-ray diffraction;
(v) a crystal of 6SL sodium salt n-hydrate which further has peaks at di action angles (2θ) of 17.8±0.2°, 14.5±0.2°, 17.4±0.2°, 19.7±0.2°, and 24.6±0.2° in addition to the peaks at the diffraction angles (2θ) described in (iv) in powder X-ray diffraction; and
(vi) a crystal of 6SL sodium salt n-hydrate which further has peaks at diffraction angles (2θ) of 14.9±0.2°, 18.9±0.2°, 22.1±0.2°, 28.3±0.2°, and 31.5±0.2° in addition to the peaks at the diffraction angles (2θ) described in (iv) and (v) in powder X-ray diffraction.

16. A process for producing a crystal of 6SL sodium salt n-hydrate, wherein n represents an arbitrary number of 0 to 5, and when n is 0, the crystal of 6SL sodium salt n-hydrate is 6SL sodium salt anhydrate, comprising a step of adding a crystal of 6SL sodium salt n-hydrate as a seed crystal to a 6SL aqueous solution containing sodium hydroxide or a carbonate, sulfate, nitrate, or chloride of sodium, a step of precipitating a crystal of 6SL sodium salt n-hydrate by adding or adding dropwise N,N-dimethylformamide to the aqueous solution, and a step of collecting the crystal of 6SL sodium salt n-hydrate from the aqueous solution, wherein the crystal of 6SL sodium salt n-hydrate is a crystal of 6SL sodium salt n-hydrate described in any one of the following (iv) to (vi):
(iv) a crystal of 6SL sodium salt n-hydrate which has peaks at diffraction angles (2θ) of 5.9±0.2°, 11.7±0.2°, 20.1±0.2°, 21.0±0.2°, and 23.6±0.2° in powder X-ray diffraction;
(v) a crystal of 6SL sodium salt n-hydrate which further has peaks at diffraction angles (2θ) of 17.8±0.2°, 14.5±0.2°, 17.4±0.2°, 19.7±0.2°, and 24.6±0.2° in addition to the peaks at the diffraction angles (2θ) described in (iv) in powder X-ray diffraction; and
(vi) a crystal of 6SL sodium salt n-hydrate which further has peaks at diffraction angles (2θ) of 14.9±0.2°, 18.9±0.2°, 22.1±0.2°, 28.3±0.2°, and 31.5±0.2° in addition to the peaks at the diffraction angles (2θ) described in (iv) and (v) in powder X-ray diffraction.

17. The crystal according to claim 1, wherein the crystal is a crystal of 6SL sodium salt 2.5-hydrate 0.5-methanol solvate.

18. The crystal according to claim 17, wherein the crystal has the following approximate unit cell parameters when measured at −173° C. in single crystal X-ray structure analysis: a=9.0695 Å; b=12.4146 Å; c=14.6177 Å; α=71.326°; β=79.972°; γ=14.6177°; V=1533.3 Å$^3$; and Z=1, and has a space group of P1.

* * * * *